US011986161B2

(12) United States Patent
Noyes et al.

(10) Patent No.: US 11,986,161 B2
(45) Date of Patent: May 21, 2024

(54) DETACHABLE ENDOSCOPE SHAFT

(71) Applicant: ResnENT, LLC, Bloomington, IL (US)

(72) Inventors: Willard S. Noyes, Bloomington, IL (US); Benjamin Joseph Gray, Portland, ME (US)

(73) Assignee: RESNENT, LLC, Bloomington, IL (US)

( * ) Notice: Subject to any disclaimer, the term of this patent is extended or adjusted under 35 U.S.C. 154(b) by 0 days.

(21) Appl. No.: 18/198,107

(22) Filed: May 16, 2023

(65) Prior Publication Data

US 2023/0284887 A1    Sep. 14, 2023

Related U.S. Application Data

(62) Division of application No. 17/967,770, filed on Oct. 17, 2022, now Pat. No. 11,771,312.

(60) Provisional application No. 63/256,390, filed on Oct. 15, 2021.

(51) Int. Cl.
*A61B 1/05* (2006.01)
*A61B 1/00* (2006.01)
*A61B 1/06* (2006.01)

(52) U.S. Cl.
CPC ............ *A61B 1/05* (2013.01); *A61B 1/00121* (2013.01); *A61B 1/0684* (2013.01)

(58) Field of Classification Search
CPC ... A61B 1/00105; A61B 1/00121; A61B 1/05; A61B 1/0685
See application file for complete search history.

(56) References Cited

U.S. PATENT DOCUMENTS

| 8,419,623 | B2 | 4/2013 | Garcia et al. |
| 8,920,309 | B2 | 12/2014 | Boulnois et al. |
| 9,107,573 | B2 | 8/2015 | Birnkrant |
| 9,161,769 | B2 | 10/2015 | Stoddard et al. |

(Continued)

FOREIGN PATENT DOCUMENTS

| DE | 102010034623 A1 | 2/2012 |
| EP | 3146927 A1 | 3/2017 |
| WO | WO 2022/003569 A1 | 1/2022 |

OTHER PUBLICATIONS

Witt et al., "Types of Sialendoscopes and Accessories-Diagnostic Sialendoscopy: Polydiagnost Modular Endoscope," Surgery of the Salivary Glands (2021), 7 pages.

(Continued)

*Primary Examiner* — Aaron B Fairchild
(74) *Attorney, Agent, or Firm* — Sheppard, Mullin, Richter & Hampton LLP

(57) ABSTRACT

Some implementations of the disclosure are directed to detachable endoscope shafts assemblies including detachable endoscope shafts. In one implementation, an endoscope assembly comprises: an endoscope housing comprising a distal connector including first circuitry configured to receive one or more image signals or supply power from the endoscope housing; and a detachable endoscope shaft comprising: a distal segment configured to be inserted in a patient cavity; an attachment segment proximal to the distal segment, the attachment segment configured to be removably coupled to an instrument or adapter; and a proximal connector configured to removably and electrically couple to the distal connector, the proximal connector including second circuitry configured to electrically couple to the first circuitry.

20 Claims, 23 Drawing Sheets

(56) References Cited

U.S. PATENT DOCUMENTS

| | | |
|---|---|---|
| 9,386,914 B2 | 7/2016 | Birnkrant et al. |
| 9,717,399 B2 | 8/2017 | Newman |
| 10,512,391 B2 | 12/2019 | Noyes |
| 10,674,897 B2 | 6/2020 | Levy |
| 11,291,357 B2 | 4/2022 | Levy et al. |
| 2005/0191046 A1 | 9/2005 | Dehmel et al. |
| 2018/0206707 A9 | 7/2018 | Ouyang et al. |
| 2018/0256009 A1 | 9/2018 | Ouyang et al. |
| 2018/0326144 A1 | 11/2018 | Truckai |
| 2019/0313881 A1 | 10/2019 | Francher |
| 2019/0374095 A1 | 12/2019 | Lord et al. |

OTHER PUBLICATIONS

International Search Report and Written Opinion dated Feb. 8, 2023 for International Application No. PCT/US2022/046914, filed Oct. 17, 2022.

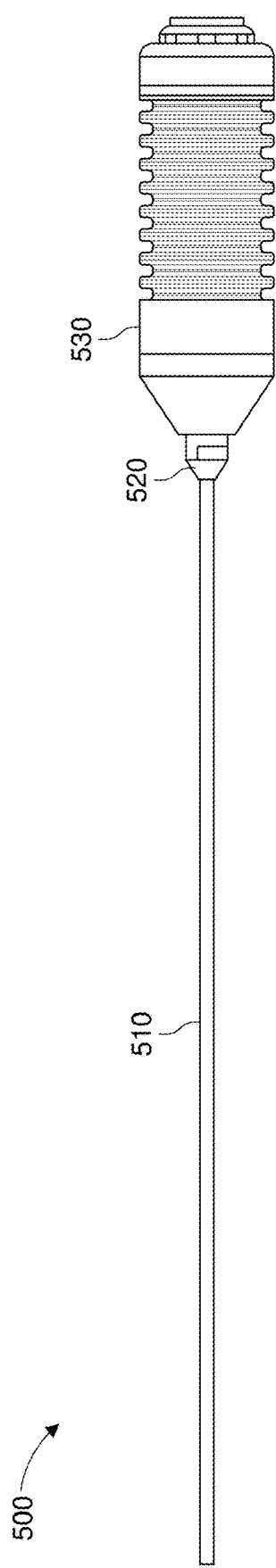
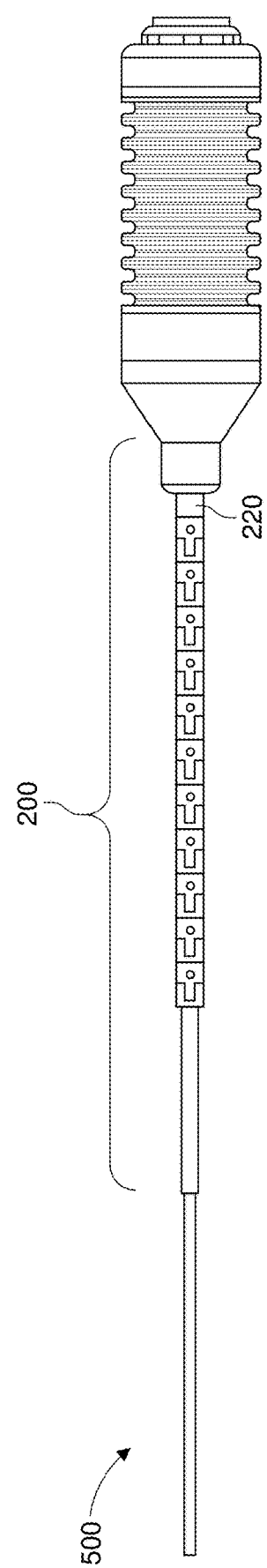
FIG. 3A
FIG. 3B

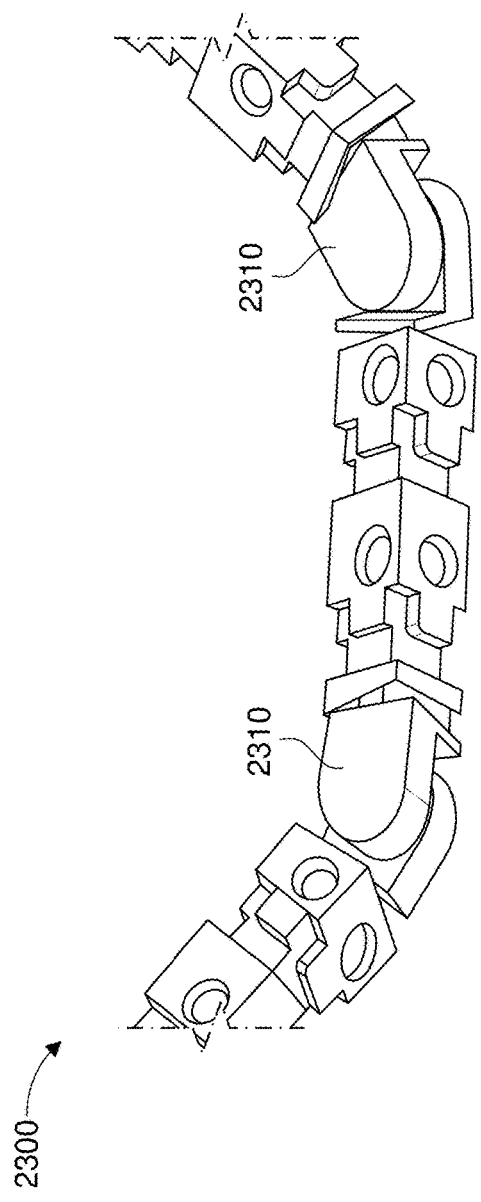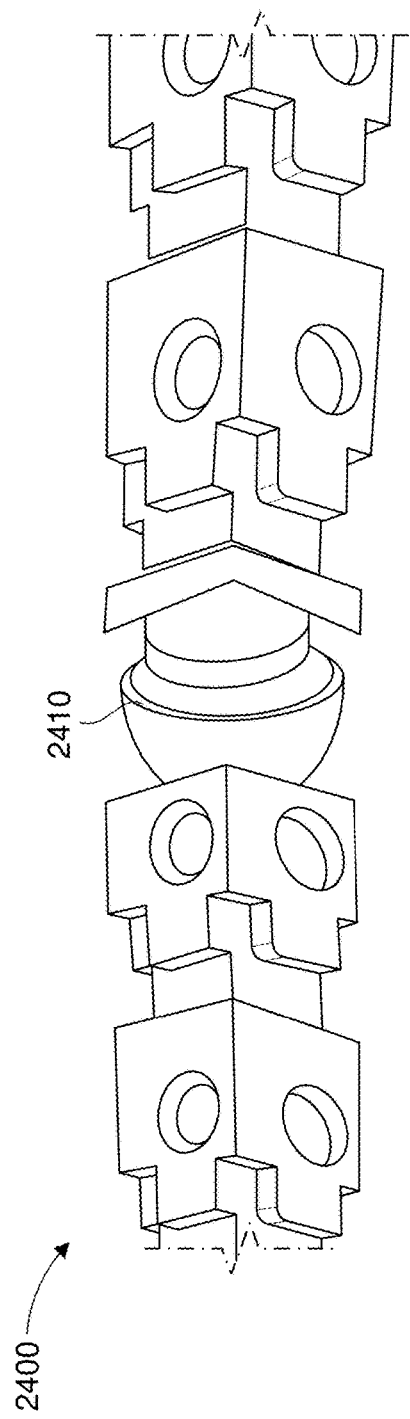

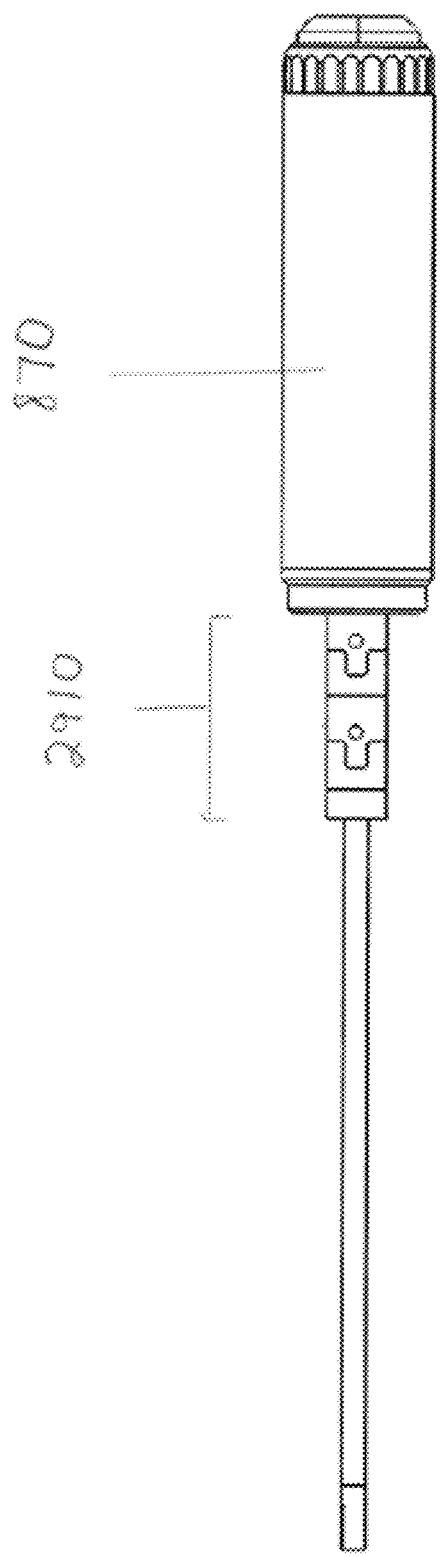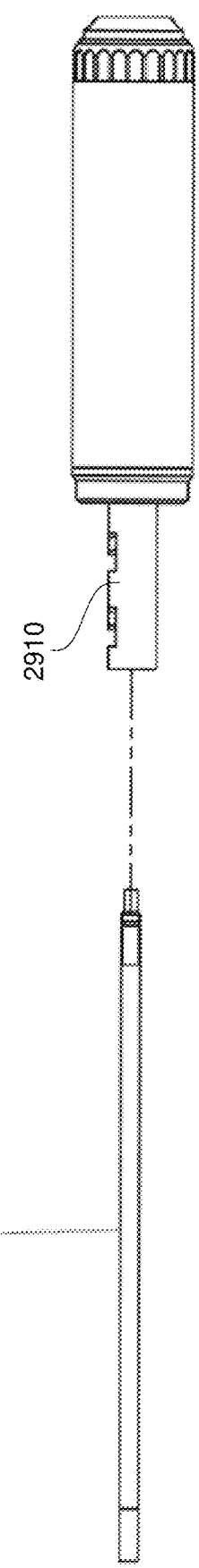
FIG. 16C
FIG. 16D

DETACHABLE ENDOSCOPE SHAFT

CROSS-REFERENCE TO RELATED APPLICATION

The present application is a divisional of and claims priority to U.S. patent application Ser. No. 17/967,770 filed Oct. 17, 2022, issued as U.S. Pat. No. 11,771,312 on Oct. 3, 2023, and titled "DETACHABLE ENDOSCOPE SHAFT", which claims priority to U.S. Provisional Patent Application No. 63/256,390 filed on Oct. 15, 2021 and titled "DETACHABLE ENDOSCOPE SHAFT WITH IMAGE SENSOR". The entire content of the above referenced applications is incorporated herein by reference.

BACKGROUND

Endoscopes are illuminated tubular instruments with eyepieces or cameras that are used to look inside a body cavity in procedures called an endoscopy. During performance of a medical procedure with an instrument that is inserted within a patient's body cavity, endoscopes may be used to visualize the medical instrument and body cavity during the procedure. For example, the endoscope may be used to allow the physician to view tissue or other matter within a cavity or anatomic space in a patient while using suction or grasping forceps to remove tissue from the space.

In procedures that utilize medical instruments in combination with endoscopes, the endoscope is typically a rigid or flexible tool that is manipulated separately from the medical instrument. During the procedure, medical personnel hold and guide the endoscope with one hand and the instrument used to treat the patient with the other hand. Depending on the anatomic space to be visualized, physicians will use either a rigid or flexible endoscope. For example, pulmonologists and gastroenterologists use flexible endoscopes and orthopedic surgeons typically use rigid endoscopes, whereas otolaryngologists use either rigid or flexible scopes depending on the surgical application. When using endoscopes with other surgical instrumentation within a confined space, there is often interference between the endoscope and instrument when trying to manipulate within the same anatomic space. This is sometimes referred to as "sword fighting" and can make surgeries technically more difficult and sometimes require another incision or access port to overcome. This is particularly true in orthopedic arthroscopy or when operating in the posterior nasal cavity.

Current implementations of rigid endoscopes have significant limitations with respect to visualizing the patient's body cavity during a procedure. Angled rigid scope visualization often distorts the surgeon's perspective and is cumbersome to use in conjunction with secondary instruments. The surgeon is often handicapped by the rigidity of the endoscope and the angle of visualization when trying to perform tasks in small cavities or in areas difficult to reach with instruments. This is particularly true when trying to operate within the frontal and maxillary sinuses. In pediatric cases, there is often not enough room to insert multiple instruments into a nasal passage or sinus opening at the same time. In addition, during direct laryngoscopy procedures, multiple instruments inserted into the lumen of a rigid laryngoscope makes direct visualization around the endoscope, camera attachment, and instrumentation very difficult.

Likewise, current implementations of flexible endoscopes present their own set of problems. In some current flexible endoscopic systems on the market, a tool is advanced through a tiny instrument channel incorporated within the length of a flexible endoscope. In such systems, the size of the tool is limited to the diameter of the endoscopic channel, and thus greatly limits the tool sizes and options available for endoscopic tissue manipulation. Externally attaching a conventional flexible endoscope to a surgical instrument or device is difficult because the endoscope body is difficult to stabilize, the endoscope hangs off the back of the instrument, and the endoscope does not connect or transfer easily from one instrument to another. Use of currently available flexible endoscopes requires two hands: one hand to manipulate the tip flexion and another hand to stabilize the tip the flexible shaft.

As noted above, current implementations of endoscopes have limitations with respect to their usage with other instruments during procedures. Rigid endoscopes cannot be bent to effectively visualize a body cavity of the patient, and flexible endoscopes cannot be effectively stabilized or easily used in combination with other internal or externally applied instrumentation. In many cases, it may be difficult for the endoscope to visualize the grasping or removing of tissues, and in some hard to reach areas such as the maxillary and frontal sinuses, such a procedure is often done blindly, resulting in incomplete tissue removal.

In order to overcome some of these limitations in flexible and rigid endoscope design and functionality, U.S. Pat. No. 10,512,391 introduced an improved flexible-rigid hybrid design for an endoscope with instrument attachment capabilities for removably coupling and decoupling the endoscope to a proximal handle portion and/or a distal tool portion of a variety of different surgical instruments. The remains however continued need for newer and simplified methods for attachment of endoscopes to various surgical instruments across numerous surgical specialties.

SUMMARY

The current disclosure describes different attachment mechanisms for attaching an endoscope shaft to various instrumentation. The manner in which an endoscope shaft can be modified, either permanently or temporarily to allow for quick attachment to an instrument (e.g., surgical tool) is further detailed below. Additionally, various adapters are presented that would facilitate attachment of the endoscope shafts to surgical instrumentation. Different instrument types and the modifications necessary to allow endoscope attachment are also provided. Furthermore, various endoscope assemblies with detachable endoscope shafts are also described herein.

There is a need for improved mechanisms for attaching different types of endoscopes to instruments. To this end, implementations of the present disclosure are directed toward endoscope shaft design and attachment adapters that may be removably or permanently coupled to an endoscope or surgical instrument in a variety of manners and configurations.

As further described below, an endoscope shaft attachment adapter may be advanced over the shaft of the endoscope and secured at a proximal end of the endoscope shaft (e.g., by connecting it to the distal end of the endoscope handle/scope head). This endoscope attachment "sleeve" adapter includes a rigid attachment segment including means for coupling the endoscope to an instrument in a plurality of lengthwise positions. The endoscope attachment adapter may also be configured such that the endoscope may be attached to the instrument in a plurality of different circumferential positions. For example, the endoscope attachment adapter may be configured to rotate about its longitudinal axis, and/or the endoscope attachment adapter may have attachment means circumferentially spaced about the rigid attachment segment.

Although the channel housing attachment mechanism described in U.S. Pat. No. 10,512,391 is functional and most often adequate, it can allow for excess movement of the scope within the channel secondary to inherent play in the movement of the lever arm as it engages with the scope. In addition, it may require an excessively elongated channel to accommodate the mechanical action and length of a side button and scope engagement lever.

Initially described for use with a hybrid, rigid/flexible endoscope, the ability to adapt conventional rigid or flexible endoscopes to work with the attachment mechanism described in U.S. Pat. No. 10,512,391 would be advantageous. Prior disclosure shows the slotted/grooved, rectangular, proximal attachment portion of the endoscope shaft to be a rigid extension of the endoscope housing. Endoscopes of conventional design that do not contain this proximal shaft attachment configuration typically have a smooth, circumferential shaft making attachment to instrumentation difficult. Such conventional endoscopes would require an adapter sleeve to convert the smooth endoscope shaft to a shape and configuration that would allow attachment to instrumentation in a manner similar to that previously described. These attachment adapter sleeves could slide over the smooth endoscope shaft and fixate to the endoscope housing via a coupler. Different embodiments may require sleeve adapters that are rigid, malleable, articulating, or flexible.

When externally attaching an endoscope to a surgical device, the orientation of the image in relation to the scope and instrument handle must be maintained or adjusted as necessary to maintain adequate user display orientation. If the user rotates the handle position then the image will rotate accordingly because the endoscope is fixated to the instrument devise. Having the ability to mechanically rotate and reorient an image while an endoscope is fixated to a surgical tool via the attachment mechanisms described herein would also be beneficial. Such applications would require the endoscope shaft, whether rigid, flexible, or hybrid, to circumferentially rotate within the sleeve adapter depending on the application.

The present disclosure also includes scope shafts that are either removably or permanently fixed to the endoscope housing. Such endoscopes and endoscope shaft configurations could be made disposable or remain reusable and would contain the optical and mechanical configurations necessary to allow instrument attachment and transference of the optical signal from the distal tip of the endoscope through to the proximal endoscope housing. Removable shafts, sleeve adapters, or permanent shaft designs that act to alter the shape, angulation, or configuration of the scope shaft, convert a flexible scope shaft (or portion thereof) to a more rigid scope shaft, or convert a flexible or hybrid shaft into a hinged shaft utilizing single or multiple hinged units are also envisioned. A hinged endoscope, created either as a one-piece fabricated unit or the result of a removable hinged shaft or hinged sleeve adapter would allow adjustable angulation of the endoscope housing away from the long axis of the endoscope shaft, such as would be required during direct operative laryngoscopy. A hinged shaft design might also enable scope rotation within the lumen of the hinged shaft or adapter.

Endoscope shafts of customized shape and contour might be useful when attaching the endoscope to various surgical instrument housings or devices. Such devices may include surgical coblation or plasma wands, inflation balloons, electrocautery devices, lasers, cannulas, syringes, robotic tools, articulating forceps, articulating cannulas, ultrasound probes, surgical staplers, snares, etc. The irregular shape or contour of these instrument devices/housings could impede attachment of the endoscope shaft and attached endoscope housing to the instrument and therefore interfere with proper instrument use, mechanics, or line of sight visualization. Significant re-engineering of existent instrument devices with profiles unable to accommodate the linear nature of the endoscope may need to occur.

Re-engineering expenses may prohibit instrument manufacturers from making necessary design modifications to allow for endoscope attachment. A channel adapter that is capable of receiving and securing the endoscope shaft both proximally and/or distally could be clipped to such devices in a customized manner and would make this endeavor more feasible and cost effective.

By virtue of using the endoscope attachment adapters described herein, various technical advantages may be realized. First, the adapters may be used to retrofit existing endoscopes, rigid or flexible, with a rigid attachment segment. The adapter, when retrofitted over the endoscope, may provide for improved and simplified mechanism for removably coupling and decoupling the endoscope to a variety of different instruments. For example, the adapter may be retrofitted over an existing flexible endoscope to convert it to a flexible-rigid hybrid endoscope having the benefits of a flexible distal shaft segment and rigid proximal shaft segment with an instrument attachment mechanism.

The retrofitted adapter may provide a variety of advantages to both physicians and patients. For example, by providing a quick, simplified, and reliable mechanism for removably coupling an endoscope to an instrument, the adapter may save the physician and patient time. Additionally, the adapters described herein may be adapted to be removably coupled to a variety of different instrument types, which may provide additional cost savings and convenience. It may allow for the physician to use an endoscope with a variety of different instruments in a one-handed manner to facilitate a patient procedure. Removable, disposable endoscope and adapter shaft configurations would avoid the need for repeat sterilization and therefore increase operating room efficiency and case turn around. In some cases, this may eliminate the requirement of having a second medical person to help with the procedure, and may permit more office-based surgeries, which may reduce the cost of various procedures.

Further still, the adapter designs and shaft configurations described herein may improve patient comfort by eliminating the need to separately insert an endoscope and instrument into a body orifice (e.g., nose or throat) at the same time. Moreover, the adapter design may improve surgical access, visualization, and instrumentation within conventionally hard to reach anatomic places such as the nasopharynx, frontal sinus, anterior maxillary sinus, tongue base, orthopedic joint space, uterus, abdomen, bladder, etc.

In further implementations, the rigid attachment segment of the endoscope shaft or sleeve adapter may include an improved design for engaging the endoscope in an instrument channel.

In yet further implementations, the rigid attachment segment of the shaft or sleeve adapter may be hinged, allowing for changes in the shape of the rigid shaft to accommodate varying shapes and contours of surgical instruments without allowing for flaccidity which would destabilize the scope when attached to an instrument.

In yet further implementations, sleeve adapters to provide suction and/or irrigation to the endoscope tip or to facilitate attachment of the distal aspect of an endoscope shaft, whether flexible or rigid, to an instrument or instrument shaft are also described.

In yet further implementations, a disposable and/or removable rigid, flexible, or hybrid endoscope shaft may insert into an otherwise disposable or reusable endoscope housing or rigid attachment segment extending from the housing. The disposable shafts may include various instrument channel connectors for the attachment of external instrument configurations to the distal or proximal endoscope shaft. In other embodiments, the removable endoscope shafts may include other adapter features described herein. For example, suction or irrigation channels may be incorporated into the removable shaft. Some disposable shafts might be hinged, malleable, articulating, or irregularly contoured, etc. Combining one or more adapter features into an disposable endoscope shaft that is instrument attachable may obviate the need to utilize additional adapters.

In one embodiment, an endoscope comprises: a housing comprising a light source and circuitry for receiving an image signal; a proximal attachment segment coupled to and extending from the housing, the proximal attachment segment configured to be removably coupled to an instrument or adapter; and a detachable endoscope shaft configured to be optically, electrically, and mechanically coupled to a distal end of the proximal attachment segment such that the endoscope shaft receives light transmitted by the light source and transmits the image signal to the circuitry.

In some implementations, an interior of the distal end of the proximal attachment segment, comprises: a first illumination coupling for optically coupling a second illumination coupling of the detachable endoscope shaft to the light source; and one or more first electrical contacts; and a proximal end of the detachable endoscope shaft comprises an endoscope connector segment, including: the second illumination coupling; and an image module connector comprising one or more second electrical contacts configured to contact the one or more first electrical contacts to form an electrical connection between the circuitry of the housing and the detachable endoscope shaft.

In some implementations, the distal end of the proximal attachment segment further comprises a receptacle; and the endoscope connector segment further comprises: a mechanical connector configured to enable a snap-in connection to the receptacle.

In some implementations, a distal end of the detachable endoscope shaft comprises an image sensor electrically coupled to the one or more second electrical contacts.

In some implementations, the proximal attachment segment is a rigid attachment segment, the surface of the rigid attachment segment comprising a groove and a section adjacent the groove, the section protruding relative to the groove and comprising a recessed indentation or protrusion.

In some implementations, the proximal attachment segment is a rigid attachment segment, the surface of the rigid attachment segment comprising multiple grooves and multiple sections alternating along the longitudinal length of the rigid attachment segment; each of the sections protrudes relative to the grooves and comprises a recessed indentation or protrusion; and the multiple sections and the multiple grooves are configured such that the instrument or the adapter can be coupled to the endoscope in a plurality of lengthwise positions.

In some implementations, the rigid attachment segment is fixed to the housing.

In some implementations, the rigid attachment segment is removably coupled to the housing via an adapter.

In some implementations, the rigid attachment segment is rotatable about its longitudinal axis.

In one embodiment, a detachable endoscope shaft comprises: a distal end including an image sensor; and a proximal end including an endoscope connector segment configured to removably, mechanically, electrically, and optically couple the endoscope shaft to an endoscope housing, the endoscope connector segment comprising: an illumination coupling for optically coupling the detachable endoscope shaft to a light source of the endoscope housing; and an image module connector comprising one or more first electrical contacts electrically coupled to the image sensor, the one or more first electrical contacts configured to contact one or more second electrical contacts to form an electrical connection between circuitry of the endoscope housing and the detachable endoscope shaft.

In some implementations, the detachable endoscope shaft further comprises an illumination channel that begins at the illumination coupling and ends at an opening at the distal end of the endoscope shaft, the opening at the distal end adapted to emit light to illuminate a sample, and the image sensor adapted to collect light reflected by the sample.

In some implementations, the detachable endoscope shaft further comprises an attachment segment distal to the endoscope connector segment, the attachment segment configured to be removably coupled to an instrument or adapter.

In some implementations, the attachment segment is a rigid attachment segment, the surface of the rigid attachment segment comprising a groove and a section adjacent the groove, the section protruding relative to the groove and comprising a recessed indentation or protrusion.

In some implementations, the attachment segment is a rigid attachment segment, the surface of the rigid attachment segment comprising multiple grooves and multiple sections alternating along the longitudinal length of the rigid attachment segment; each of the sections protrudes relative to the grooves and comprises a recessed indentation or protrusion; and the multiple sections and the multiple grooves are configured such that the instrument or the adapter can be coupled to the endoscope in a plurality of lengthwise positions.

In some implementations, the endoscope connector segment further comprises: a mechanical connector configured to enable a snap-in connection.

In some implementations, the mechanical connector comprises a circumferential groove that allows for the snap-in connection to a receptacle.

In some implementations, the mechanical connector comprises an elongated rectangular protrusion along a surface of the endoscope connector segment.

In one embodiment, an endoscope assembly comprises: an endoscope housing comprising a distal connector including first circuitry configured to receive one or more image signals or supply power from the endoscope housing; and a detachable endoscope shaft comprising: a distal segment configured to be inserted in a patient cavity; an attachment segment proximal to the distal segment, the attachment segment configured to be removably coupled to an instrument or adapter; and a proximal connector configured to removably and electrically couple to the distal connector, the proximal connector including second circuitry configured to electrically couple to the first circuitry.

In some implementations, the detachable endoscope shaft further comprises one or more image sensors configured to generate the one or more image signals; the second circuitry is configured to transmit the one or more image signals to the first circuitry; and the first circuitry is configured to receive the one or more image signals.

In some implementations, the one or more image signals comprise a first image signal and a second image signal; the one or more image sensors comprise a first image sensor to generate the first image signal and a second image sensor to generate the second image signal; the first circuitry comprises one or more first electrical contacts to receive the first image signal and one or more second electrical contacts to receive the second image signal; the second circuitry comprises one or more third electrical contacts to transmit the first image signal and one or more fourth electrical contacts to transmit the second image signal; the one or more first electrical contacts and the one or more third electrical contacts are to removably couple; and the one or more second electrical contacts and the one or more fourth electrical contacts are to removably couple.

In some implementations, the first circuitry comprises first and second sets of opposing electrical contacts, and the second circuitry comprises a third set of electrical contacts configured to slidably connect between the first and second sets of opposing electrical contacts.

In some implementations, the endoscope housing further comprises a light source; and the distal connector further includes an illumination coupling to optically couple the light source to the detachable endoscope shaft via the proximal connector.

In some implementations, the distal connector further includes a groove or protrusion to mechanically couple the distal connector to the proximal connector.

In some implementations, the endoscope assembly further comprises a sleeve adapter to removably couple to the detachable endoscope shaft, the sleeve adapter comprising: a proximal connector to couple to the attachment segment; and a cannula distally extending from the proximal connector, the distal segment being slid through the cannula when the sleeve adapter is removably coupled to the detachable endoscope shaft.

In some implementations, the cannula of the sleeve adapter is stiffer than the distal segment, the cannula configured to facilitate guiding the detachable endoscope shaft.

In some implementations, the sleeve adapter further comprises a suction or irrigation port coupled to an inside of the cannula.

In some implementations, the attachment segment comprises first repeating features to couple to the instrument in one or more lengthwise positions; and the sleeve adapter further comprises second repeating features to couple to the instrument in one or more additional lengthwise positions.

In some implementations, the distal segment comprises one or more light sources; and when the first circuitry is electrically coupled to the second circuitry, the first circuitry is configured to supply power from the endoscope housing to the detachable endoscope shaft to power the one or more light sources.

In some implementations, the first circuitry is configured to both receive the one or more image signals and supply power from the endoscope housing to the detachable endoscope shaft to power one or more components of the detachable endoscope shaft.

In one embodiment, a detachable endoscope shaft comprises: a distal segment configured to be inserted in a patient cavity; an attachment segment proximal to the distal segment, the attachment segment configured to be removably coupled to an instrument or adapter; and a proximal connector configured to removably and electrically couple to a distal connector of an endoscope housing, the proximal connector including first circuitry configured to electrically couple to second circuitry of the endoscope housing to receive power from the endoscope housing and/or transmit one or more image signals to the endoscope housing.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

FIG. 3A shows an endoscope to which an endoscope adapter may be coupled to, with the endoscope adapter not coupled, in accordance with some implementations of the disclosure.

FIG. 3B shows the endoscope of FIG. 3A with the endoscope adapter coupled to the endoscope.

FIG. 12 shows a portion of an endoscope shaft or endoscope attachment adapter that is rectangular and includes hinged joints, in accordance with some implementations of the disclosure.

FIG. 13 shows a portion of an endoscope shaft or endoscope attachment adapter that includes a ball and socket hinge, in accordance with some implementations of the disclosure.

FIG. 16C shows a side view of the endoscope of FIG. 16A.

FIG. 16D shows a side view of the endoscope of FIG. 16A with the detachable endoscope shaft uncoupled from the rigid attachment segment of the endoscope.

The figures are not exhaustive and do not limit the present disclosure to the precise form disclosed.

DETAILED DESCRIPTION

Figure 1A:
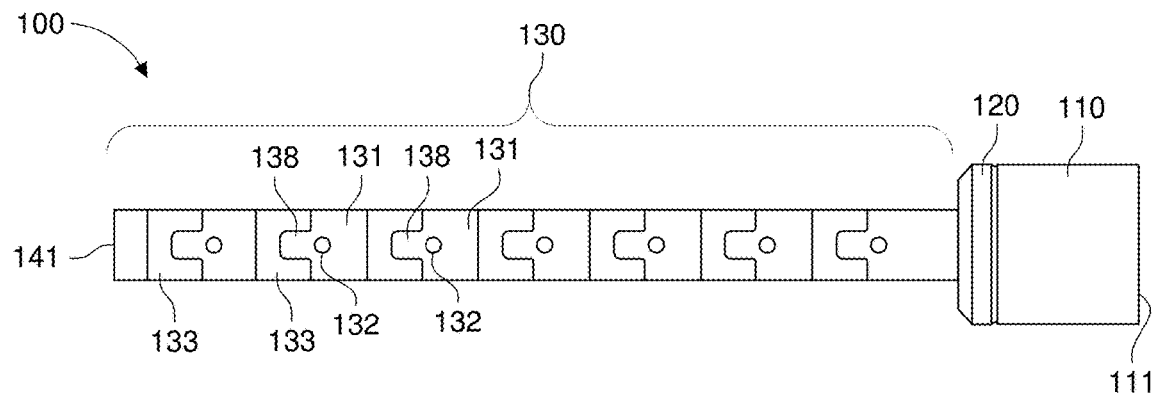
FIG. 1A shows a side view of an endoscope attachment adapter, in accordance with some implementations of the disclosure.
Figure 1B:
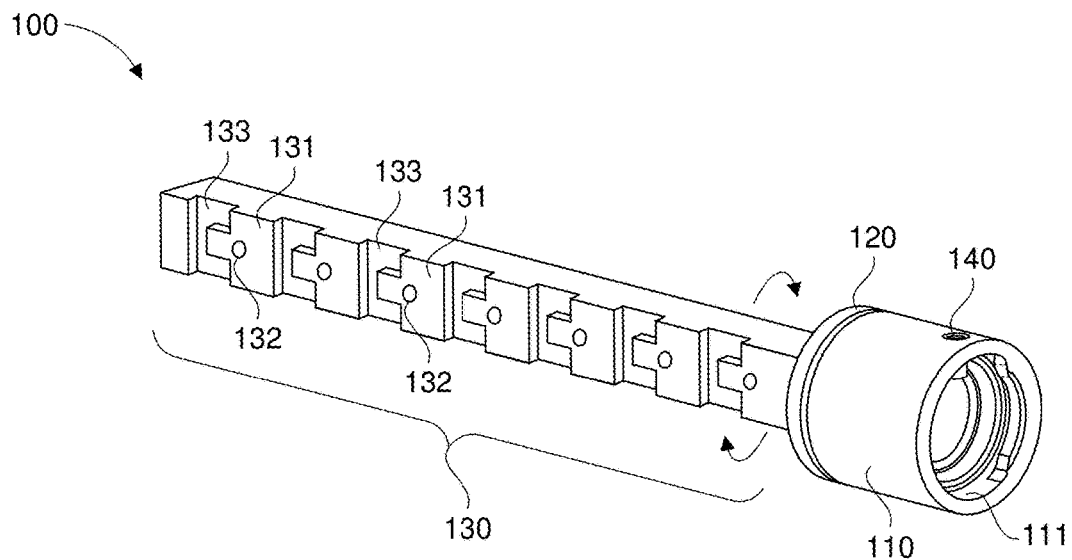
FIG. 1B shows a perspective view of the endoscope attachment adapter of FIG. 1A.
Figure 1C:
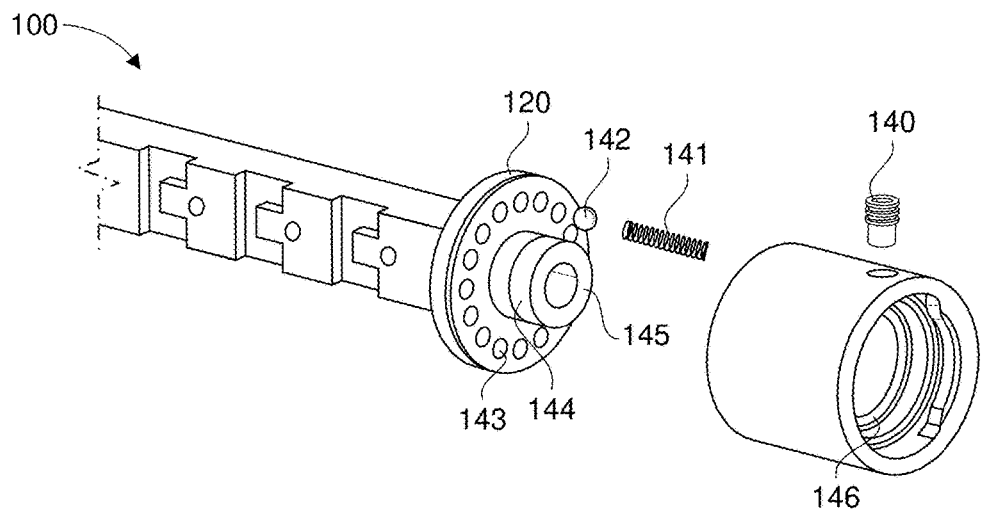
FIG. 1C shows an exploded perspective view of the endoscope attachment adapter of FIG. 1A.
Figure 1D:
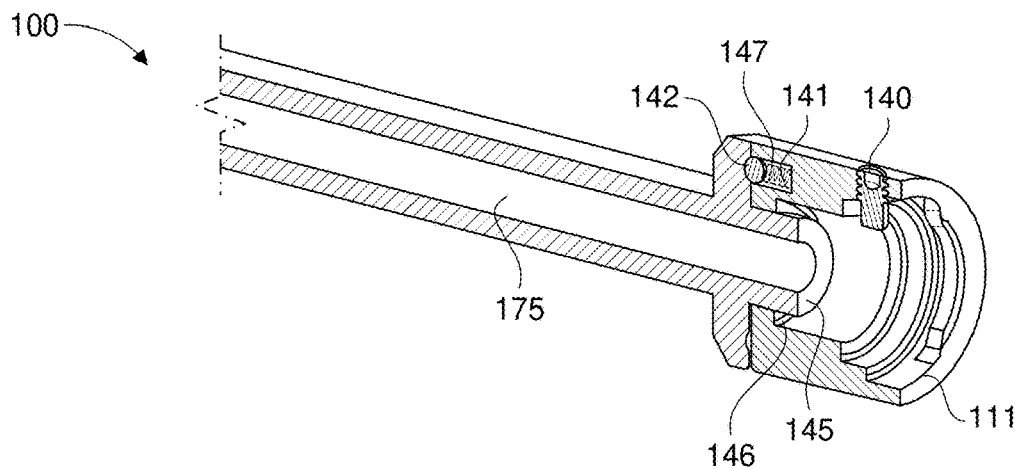
FIG. 1D shows a cross-sectional view of the endoscope attachment adapter of FIG. 1A.

FIGS. 1A-1D depict an endoscope attachment adapter 100, in accordance with some implementations of the disclosure. FIG. 1A illustrates a side view of adapter 100, FIG. 1B illustrates a perspective view of adapter 100, FIG. 1C illustrates an exploded perspective view of adapter 100, and FIG. 1D illustrates a cross-sectional view of adapter 100. Adapter 100 includes a stationary coupler 110, a rotatable joint 120, and a rigid attachment segment 130.

Ata proximal end of adapter 100 is an opening 111 through connector 110. At a distal end of adapter 100 is an opening 141. The opening 141 may begin at a distal end of rigid attachment segment 130. From opening 111 to opening 141 is a channel 175 that extends through coupler 110 and rigid attachment segment 130. A shaft of an endoscope may be threaded through channel 175, starting at opening 111 and moving through opening 141. Once the endoscope shaft is threaded through the channel of adapter 100, adapter 100 may be secured at a proximal end of the endoscope shaft by removably coupling adapter connector 110 (e.g., to an endoscope connector). The two connectors may be secured via one or more suitable coupling mechanisms, including a twist lock mechanism, an interference fit, a suction fit, a magnetic mechanism, and/or some other mechanism. Although in this example coupler 110 is illustrated as a female coupler configured to connect to a male coupler (e.g., at a proximal end of an endoscope shaft), in other implementations coupler 110 may be a male coupler configured to connect to a female coupler (e.g., at a proximal end of an endoscope shaft).

In this example, rigid attachment segment 130 is four-sided with a square cross section. In other implementations, rigid attachment segment 130 may have a different rectangular, circular, or other geometric cross section. On the surface of one of the four sides of segment 130 are formed a plurality of grooves/slots 133 and a plurality of sections 131 that protrude relative to the grooves 133, each of the sections 131 having a recessed indentation or hole 132. In this example, the plurality of grooves 133 and the plurality of sections 131 alternate along the longitudinal length of segment 130. As further described below, at least one groove 133 and at least one section 131 (e.g., a groove 133 adjacent a section 131) may be used to couple the adapter 100 to a channel of an instrument in a specific lengthwise position. In this manner, an endoscope with a secured adapter 100 may be coupled to a channel of an instrument in a specific lengthwise position. The number of grooves 133 and the number of sections 131 may depend on the desired number of lengthwise adjustments for coupling adapter 100 to an instrument, and the increment of each lengthwise adjustment. The number of grooves 133 and number of sections 131 may also depend on the width of each groove 133 and the width of each section 131. In some implementations, rigid attachment segment 130 may have between 1 and 30 grooves 133, and between 1 and 30 sections 131. In some implementations, to provide a more secure connection between the endoscope shaft (with adapter) and an instrument, multiple grooves 133 and multiple segments 131 may be used to connect to the instrument. Although grooves 133 and sections 131 are formed only on one side of segment 130 in this example, in other implementations, further described below they may be formed on two, three, or all four sides.

In alternative implementations, rigid attachment segment 130 may utilize some other suitable rigid attachment mechanism that enables attachment of an endoscope with the adapter to an instrument. For example, the adapter may utilize a magnetic attachment mechanism, a snap on attachment mechanism, a top-down ratchet mechanism, an insert ratchet mechanism, and/or an insert twist mechanism as further described in U.S. Pat. No. 10,512,391, incorporated herein by reference in its entirety. It should be noted that the disclosure is not limited to the specific attachment mechanisms described and illustrated herein, and that other mechanisms for removably coupling the flexible-rigid endoscope to an instrument are contemplated.

As depicted by FIGS. 1B-1C, a rotatable joint 120 positioned between rigid attachment segment 130 and coupler 110 enables rotation of adapter 100 about its longitudinal axis (e.g., rotation of rigid attachment segment 130 relative to coupler 110). In this manner, an endoscope may be removably coupled to an instrument via rigid attachment segment 130 in a plurality of different circumferential positions. Additionally, after coupling, the instrument may be rotated relative to the endoscope, allowing adjustment of the endoscopic image. Rotatable joint 120 may be configured to rotate continuously through 360 degrees or in stepwise degree increments. For example, depending on the desired number possible circumferential positional adjustments, it may be configured to rotate in stepwise increments of 10°, 15°, 20°, 30°, 40°, 45°, 60°, 72°, 90°, 120°, or 180°.

In this example, a coupler 110 is secured to an endoscope housing using a twist on male/female attachment mechanism. A locking screw 140 is used to secure the female coupler 110 to the male coupler of the endoscope (e.g., FIG. 3A, 520) of the endoscope housing. For example, the locking screw 140 may engage a groove in a male coupler. A rotatable, circular joint 120 is fused to the rigid attachment segment 130. The rotatable joint engages the coupler 110 by a circular extension 144 of the rigid attachment segment 130 and connector channel 175 which passes through its center. A small circumferential lip 145 on the proximal end of the circular extension 144 engages a wider circumferential lip 146 within the distal opening of the coupler housing in a manner that allows rotation movement of the joint. The circular, rotatable joint 120 contains a series of small round apertures 143 arranged on the periphery of its inner surface. The angular position of the rotatable joint is secured by a small block 142 pressed into an aperture 143 by a spring 141 contained within a channel 147 located within the coupler housing 110. When the coupler is secured to an endoscope, forceful rotation the attachment segment relative to the coupler causes the block to compress the spring as the block moves out of its occupied aperture. As the rotation continues, the compressed spring pushes the block into the next aperture thereby securing its new position.

Figure 2A:
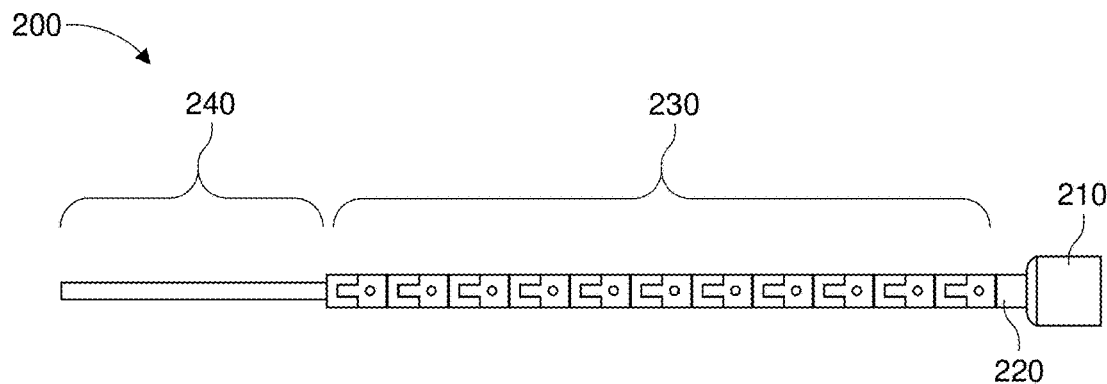
FIG. 2A illustrates a side view of another endoscope attachment adapter, in accordance with some implementations of the disclosure.
Figure 2B:
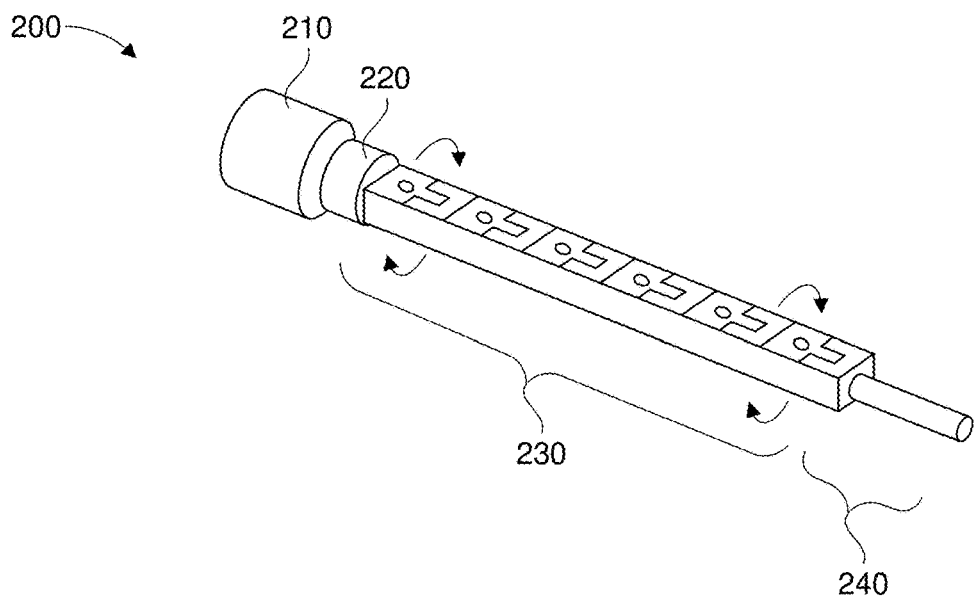
FIG. 2B shows a perspective view of the endoscope attachment adapter of FIG. 2A.

FIGS. 2A-2B illustrate another example endoscope attachment adapter 200, in accordance with implementations of the disclosure. FIG. 2A illustrates a side view of adapter 200, FIG. 2B illustrates a perspective view of adapter 200. Adapter 200 includes a stationary coupler 210, a rotatable joint 220, a rigid attachment segment 230, and a distal segment 240. The distal segment 240 may vary in length and may be rigid or flexible. In this example, the inclusion of additional distal segment 240 may help further stabilize the endoscope and attachment adapter after it is coupled to an endoscope (e.g., by threading the endoscope through a channel running through coupler 210, joint 220, rigid attachment segment 230, and distal segment 240). This may be particularly advantageous when threading the adapter over a flexible endoscope. For example, by changing the length of the distal segment 240 and rigid attachment segment 230, a flexible endoscope can be converted into a rigid endoscope or hybrid endoscope with varying lengths of rigid or flexible segments. In some implementations, the distal segment 240 may incorporate a circular indentation or other means by which other sleeve adapters more distal to itself can be secured. Such other adapters may include, but are not limited to flexible or rigid sleeve adapters that contain suction/irrigation capabilities and/or sleeve adapters that have an attached channel, tube, magnet, clip(s), suction cup(s), "zip-lock" mechanism, or other mechanism of securing the distal end of the endoscope and sleeve adapter to an instrument shaft or device.

As should be appreciated from the foregoing examples, the adapter may use any suitable mechanism (e.g., screw, slidable control, pressable control, magnetic, twist on spring tension, etc.) that may be actuated to lock the adapter onto the endoscope housing.

FIGS. 3A-3B depict an endoscope 500 to which an endoscope adapter may be coupled to, in accordance with implementations of the disclosure. The endoscope 500 includes a shaft 510, a connector 520 adjacent a proximal end of shaft 510, and an endoscope head and/or handle 530 adjacent the connector 520. Shaft 510 may rigid, flexible (e.g., bendable), removable, disposable, or it may be part rigid, flexible, or malleable (hybrid). As shown in FIG. 3B, shaft 510 may be threaded through a channel of an adapter 200 and connector 210 of adapter 200 may be secured to connector 520 of endoscope 500. Although adapter 200 is shown removably coupled to the endoscope 500 in FIG. 3B, it should be appreciated that any of aforementioned adapters (e.g., 100, 200, etc.) may be removably coupled to the endoscope 500. It should be further appreciated that any of the aforementioned adapters may either include a rotatable joint or instead be attached to the endoscope in a fixed manner incapable of manual rotation along its longitudinal axis.

In some embodiments, the endoscope shaft (flexible, rigid, or hybrid) may in and of itself be detachable and re-attachable from the endoscope head or rigid attachment segment. Such removable shafts may be capable of receiving an adapter coupler as described herein or may instead already have an adapter configuration 200 as part of their shaft structure. Detachable shaft configurations of different sizes, shapes, profiles, rigidity, and attachment segment lengths with instrument attachment capabilities would permit single use, disposable sterilized shafts and custom configurations for instrument attachment depending on the surgical application.

Once adapter 200 is secured to endoscope 500 (e.g., as depicted in FIG. 3B), endoscope 500 may be removably coupled to a channel of an instrument (further discussed below), in a plurality of different lengthwise positions via rigid attachment segment 230, and/or a plurality of different circumferential positions via rotatable joint 220. Although in this example adapter 200 includes a rotatable joint for manually rotating the endoscope for image orientation and/or positioning, alternative implementations described below describe an adapter without a rotatable joint that may instead rely on digital image rotation.

Figure 4:
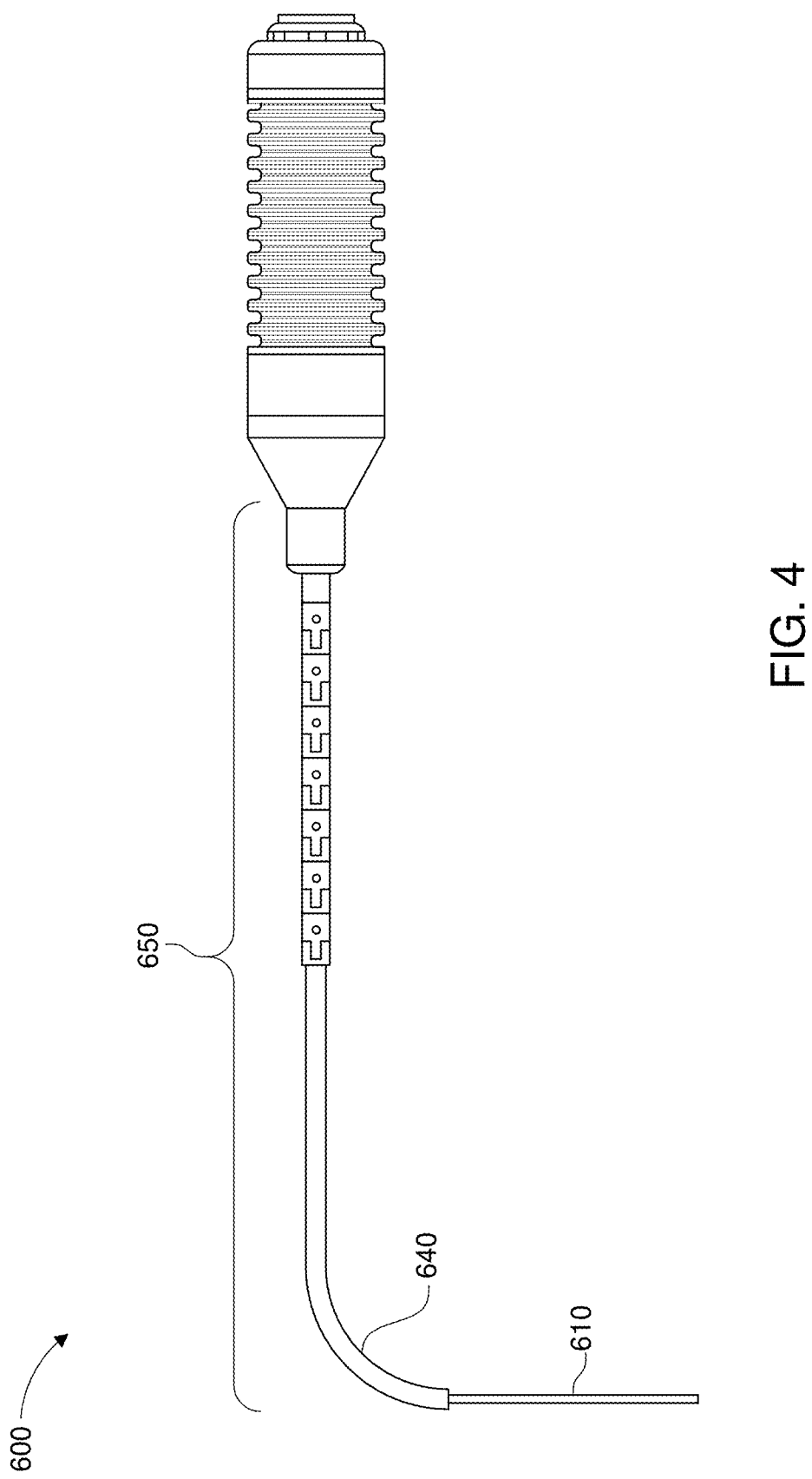
FIG. 4 shows an endoscope attachment adapter removably coupled to an endoscope with a flexible shaft, in accordance with some implementations of the disclosure.

FIG. 4 depicts an endoscope attachment adapter 650 removably coupled to an endoscope 600 with a flexible shaft 610. In this example, an angled distal part 640 of the adapter 650 causes the endoscope shaft 610 to bend 90 degrees after the adapter 650 is coupled to the endoscope. In other implementations, the endoscope shaft can take on multiple bends.

Figure 5:
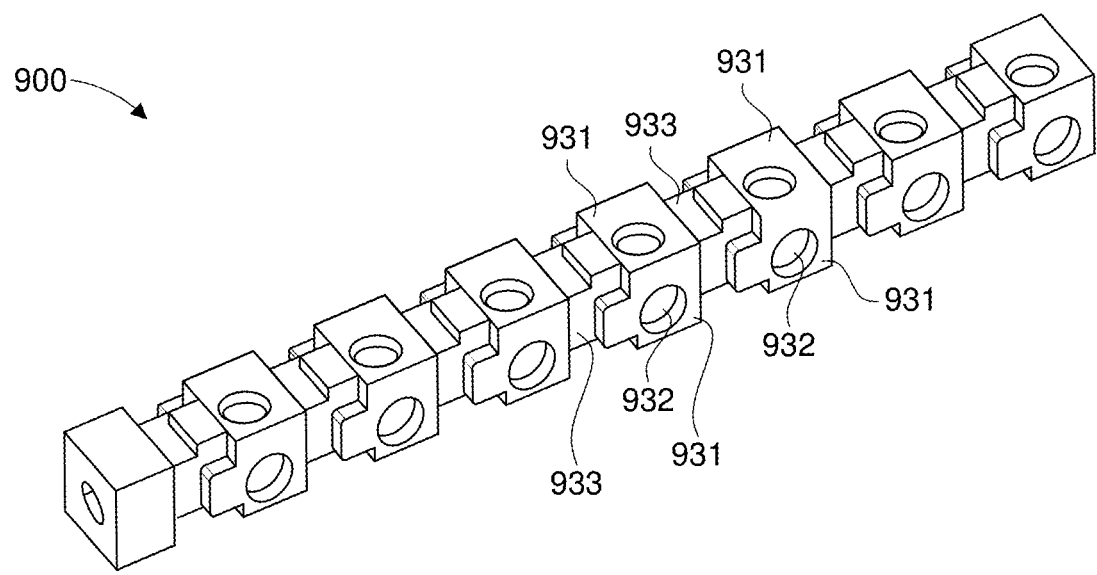
FIG. 5 shows a fixed endoscope attachment adapter, in accordance with some implementations of the disclosure.

As noted above, in some implementations, the endoscope attachment adapter may be configured to be fixed in place as opposed to being capable of rotating about its longitudinal axis. In such instances, the adapter may not include a rotatable joint (e.g., rotatable joint 120). FIG. 5 depicts one such example of a fixed endoscope attachment adapter 900. In adapter 900, the rigid attachment segment is four-sided with a square cross section. In contrast to rigid attachment segment 130, the attachment mechanism is formed on multiple sides (e.g., two, three, or all four) of the rigid attachment segment of adapter 900. That is, multiple grooves 933 and multiple sections 931, each of the sections 931 having a recessed indentation or hole 932, are formed on each of the multiple sides of the rigid attachment segment. As such, even though adapter 900 is not rotatable about a rotatable joint, it may still be used to couple an endoscope to an instrument channel in multiple circumferential positions by virtue of having the attachment segment formed on the rigid attachment segment.

Figure 6:
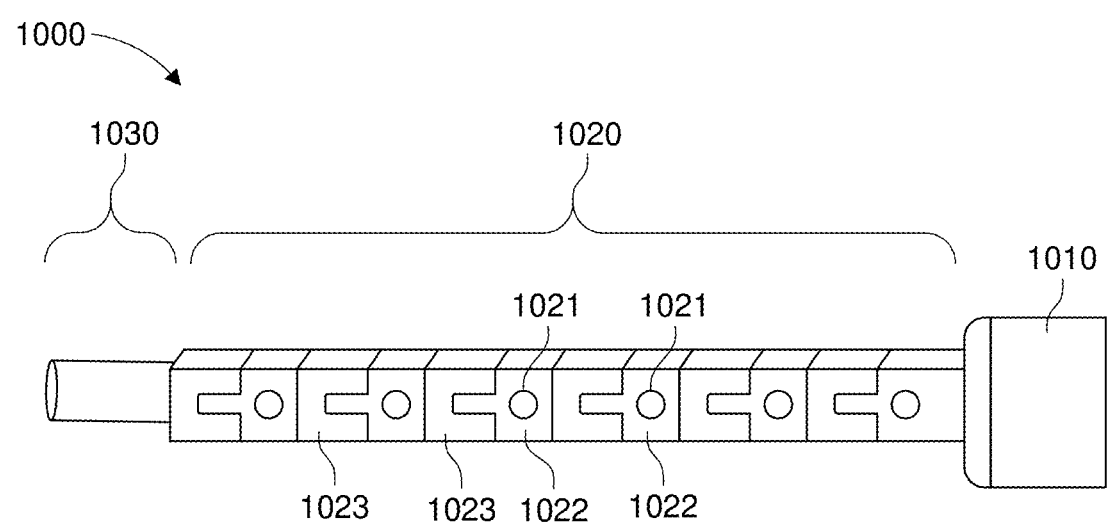
FIG. 6 shows another fixed endoscope attachment adapter, in accordance with some implementations of the disclosure.

FIG. 6 depicts another example of a fixed endoscope attachment adapter 1000. As depicted, adapter 1000 includes a connector 1010, rigid attachment segment 1020, and distal segment 1030. In some implementations, distal segment 1030 may be omitted. In adapter 1000, rigid attachment segment 1020 is four-sided with a square cross section. In contrast to rigid attachment segment 1030, the attachment mechanism is formed on multiple sides (e.g., two, three, or all four) of rigid attachment segment 1020. That is, multiple grooves 1023 and multiple sections 1022, each of the sections 1022 having a recessed indentation or hole 1021, are formed on each of the multiple sides of segment 1020. Section 1030 may in some instances be configured to receive adapter sleeves for implementing attachment of the distal scope shaft to an instrument, permitting suction/irrigation for cleaning the endoscope tip, providing a conduit for electrical current to be delivered to the scope or instrument tip, etc.

Figure 7A:
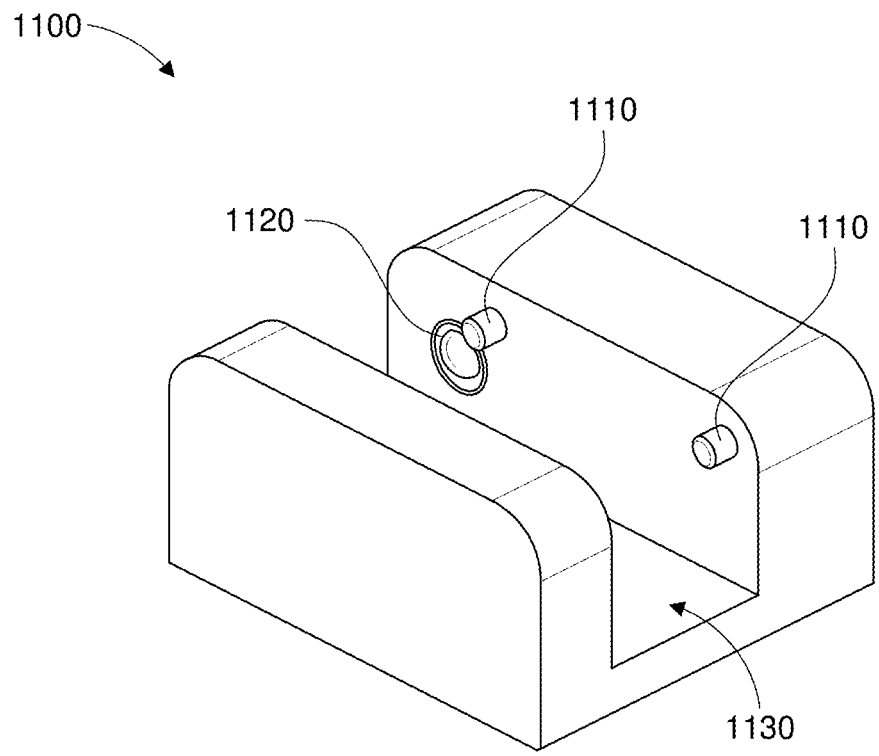
FIG. 7A shows an instrument housing that an endoscope attachment adapter may be removably coupled to, in accordance with some implementations of the disclosure.

FIG. 7A depicts an instrument housing 1100 that an endoscope attachment adapter (e.g., adapter 100) may be removably coupled to, in accordance with implementations of the disclosure. The instrument housing 1100 may be integrated near the top, on the side, or underneath the handle portion of an instrument or instrument shaft. For example, the instrument housing 1100 may be part of a handle of an instrument such as a bipolar suction cautery, coblation wand, laryngeal forceps, sinus forceps, orthopedic articulating forceps, a laryngeal syringe gun, an endoscopic Eustachian tube balloon dilator, an endoscopic tracheal dilator, an endoscopic trans-oral esophageal balloon dilator, injection syringe, or some other instrument. Housing 1100 utilizes a top-loading ratchet mechanism to secure an adapter 100 to the instrument. As such, an endoscope with a coupled adapter 100 may be removably coupled in a top-down manner by pushing down the proximal end of the endoscope shaft with the adapter (i.e., pushing down rigid attachment segment 130) into an open channel 1130 of housing 1100.

Figure 7B:
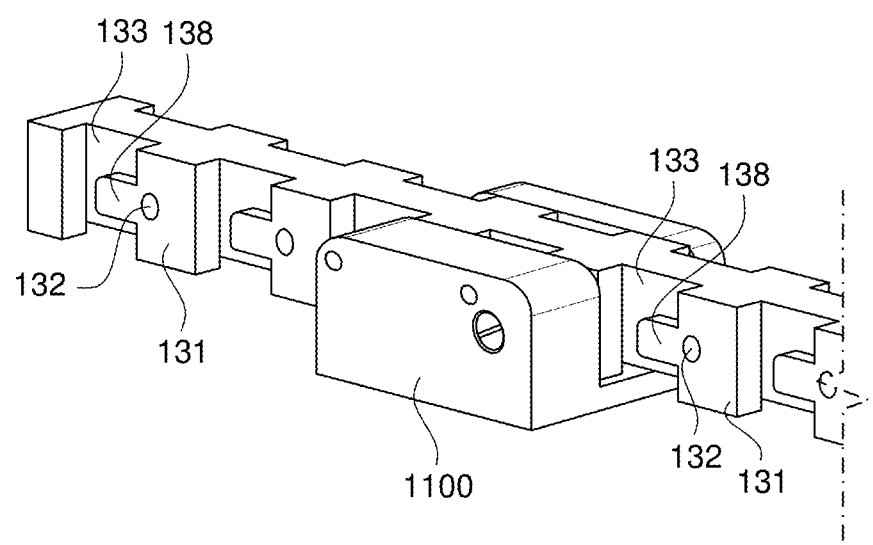
FIG. 7B shows the instrument housing of FIG. 7A removably coupled to a rigid attachment segment of an adapter, in accordance with some implementations of the disclosure.

As depicted, the interior surface of housing 1100 includes an open channel 1130, ridges, pins, or protrusions 1110, and spring-loaded protrusion (e.g., spring-loaded ball) 1120. Rigid attachment segment 130 may be secured in place by i) pushing it down into open channel 1130 along openings of two adjacent grooves 133; and ii) sliding rigid attachment segment 130 relative to open channel 1100 to position each ridge 1110 within a respective groove 133 of the adjacent grooves 133 such that protruding portions 138 of sections 131 adjacent the grooves 133 prevent lifting of the rigid attachment segment 130 (i.e., they block ridges 1110). Additionally, when the assembly is slid, spring-loaded protrusion 1120 may be secured within an indentation/hole 132 of the section 131 positioned between the two grooves 133. To reposition rigid attachment segment 130 at a different lengthwise position, the above-described operations may be reversed (i.e., it may be slid out of place, lifted off, and secured along other grooves 133). By way of illustration, FIG. 7B shows a housing 1100 removably coupled to a rigid attachment segment 130 of an adapter 100. In alternative implementations, the positions of spring-loaded protrusion 1120 and indentation/hole 132 may be reversed, i.e., the indentation 132 is part of the housing 1100 and the spring-loaded protrusion is part of the adapter 100.

By virtue of utilizing this attachment mechanism, the endoscope may be quickly secured within the instrument housing 1100 at a particular lengthwise position without the requirement of an elongated open channel 1130. This type of attachment mechanism may eliminate any rocking of the endoscope shaft within the open channel 1100 and allow for shorting of the open channel when compared to the depressible button/lever mechanism previously described in U.S. Pat. No. 10,512,391. Additionally, the top-loading ratchet mechanism described herein provides a quick and simple means for securing an endoscope to an instrument. Coupling, uncoupling, and/or repositioning an endoscope within the instrument is simply a matter of lifting down/up and sliding such that ridges 1110 are inserted into a particular set of grooves 133 and spring-loaded protrusion 1120 is secured within a particular indentation 132.

Figure 8A:
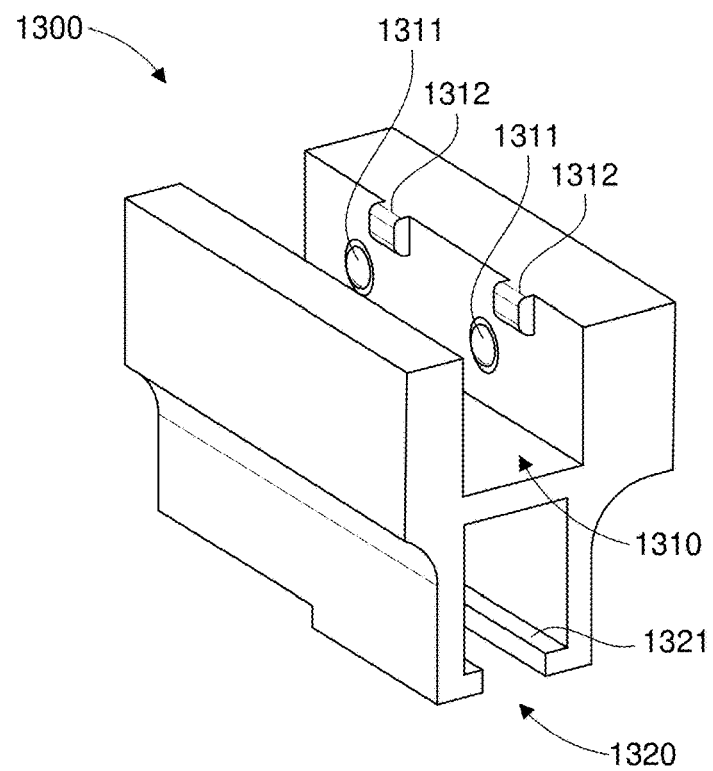
FIG. 8A shows an H-channel adapter that may be removably coupled to the attachment segment of an endoscope shaft, endoscope attachment adapter, and/or endoscope instrument tools, in accordance with some implementations of the disclosure.

FIG. 8A illustrates an H-channel adapter 1300 that may be removably coupled to the attachment segment of an endoscope shaft, endoscope attachment adapter (e.g., adapter 100), and/or endoscope instrument tools, in accordance with implementations of the disclosure. As depicted, H-channel adapter 1300 includes an upper open channel 1310 for removably coupling H-channel adapter 1300 to endoscope attachment adapter 100, and a lower open channel 1320, opposite the upper open channel 1310, for removably coupling H-channel adapter 1300 to endoscope instrument tools.

Figure 8B:
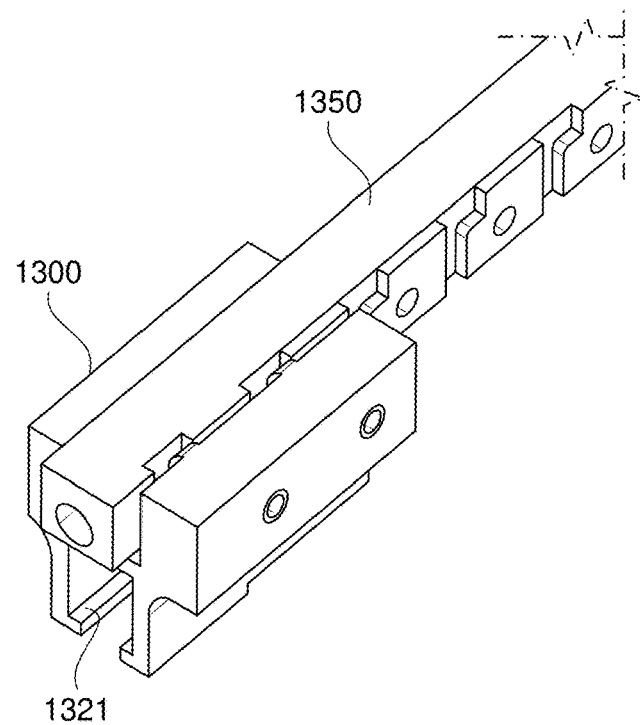
FIG. 8B shows the H-channel adapter of FIG. 8A attached to a distal end of an endoscope attachment adapter.

The interior surface of the upper open channel 1310 includes ridges or protrusions 1312, and spring-loaded protrusions (e.g., spring-loaded balls) 1311. Rigid attachment segment 130 may be secured in place by i) pushing it down into upper open channel 1310 along openings of two adjacent grooves 133; and ii) sliding rigid attachment segment 130 relative to open channel 1310 to position each ridge 1312 within a respective groove 133 of the adjacent grooves 133 such that protruding portions 138 of sections 131 adjacent the grooves 133 prevent lifting of the rigid attachment segment 130 (i.e., they block ridges 1312). Additionally, when the assembly is slid, spring-loaded protrusions 1311 may be secured within an indentation/hole 132 of the sections 131 positioned next to the two grooves 133. In certain semi-rigid or plastic channel and shaft embodiments, a rounded protrusion may suffice instead of a spring loaded protrusion. FIG. 8B depicts an example of H-channel adapter 1300 attached to a distal end of an endoscope attachment adapter 1350.

The interior surface of the lower open channel 1320 includes side rails 1321 for slidably coupling an instrument tool. For example, forceps, suctions, graspers, culture tools, fasteners, staplers, or some other instrument tool contain side grooves or longitudinal slots to engage side rails 1321 allowing attachment to the underside of the endoscope via lower open channel 1320. Although a sliding mechanism is illustrated coupling lower open channel 1320 to an instrument tool, it should be appreciated that any suitable coupling mechanism may be utilized.

By virtue of utilizing the H-channel adapter 1300 that may be removably attached to an endoscope attachment adapter (e.g., adapter 100) in a convenient lengthwise position, instrument tools may be attached in a suitable position underneath the endoscope with the adapter 100 and H-channel adapter 1300. By incorporating several instrument channels offset from one another into the same adapter, multiple instruments could be simultaneously attached to the endoscope at the same time. This would be helpful when performing rigid laryngoscopy when there may be need for a forceps, suction, laser, and endoscope all working together at the same time through a single rigid tube.

In other embodiments, other adapters may be used that have two or more channels that are offset 90 degrees from one another in an either side by side, or otherwise offset manner.

Figure 9A:
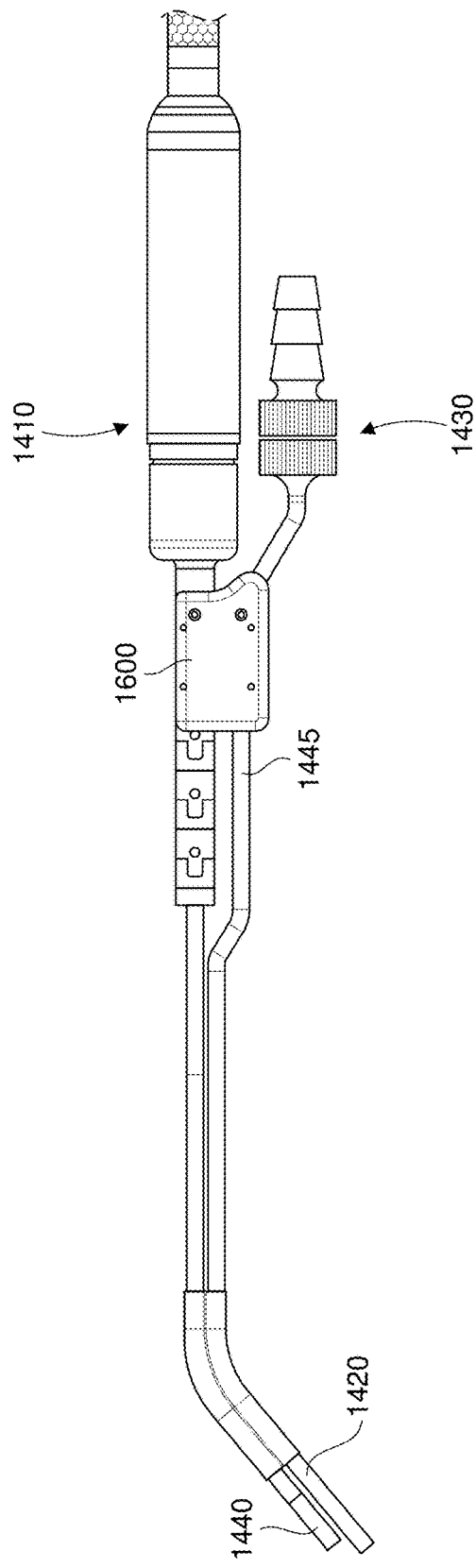
FIG. 9A shows an endoscope coupled to an instrument via an H-channel adapter, in accordance with some implementations of the disclosure.

FIG. 9A depicts an endoscope 1410 coupled to an instrument 1430 via an H-channel adapter 1600 in accordance with implementations of the disclosure. The distal shaft 1420 of the instrument 1430 is shown to extend underneath the endoscope shaft 1440. The proximal shaft 1445 of instrument 1430 connects to endoscope 1410 via H-channel adapter 1600 and a rigid attachment segment on the shaft of the endoscope (e.g., rigid attachment segment 130 of adapter 100) as discussed above. The rigid attachment segment may be part of an adapter (e.g., adapter 100) that couples to a proximal part of the shaft of the endoscope 1410 or integrated into a proximal part of the shaft of the endoscope 1410.

Figure 9B:
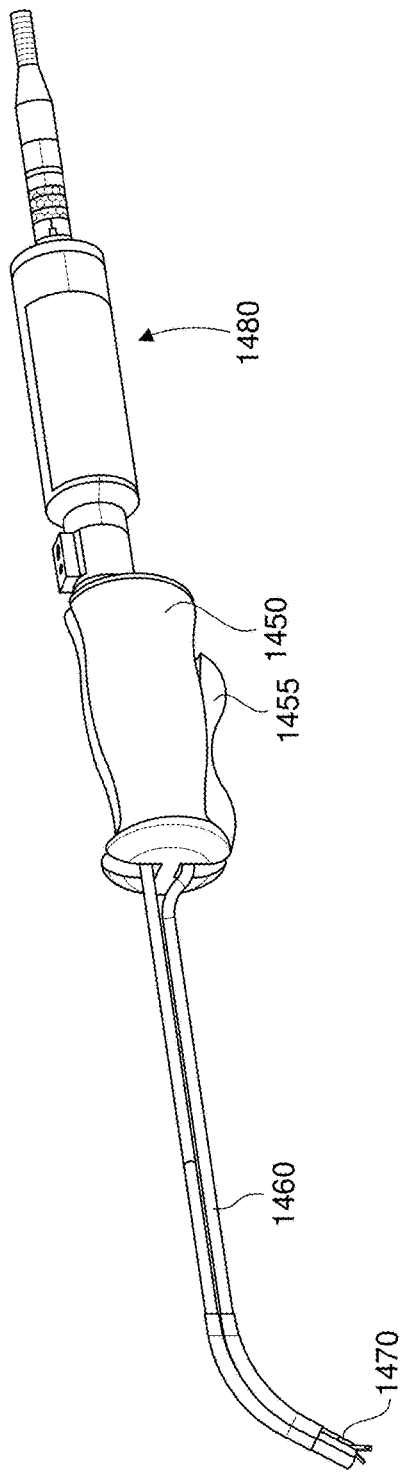
FIG. 9B shows an endoscope coupled to an instrument and instrument shaft, in accordance with some implementations of the disclosure.

FIG. 9B depicts an endoscope 1480 coupled to an instrument 1450 and instrument shaft 1460 in accordance with implementations of the disclosure. A top portion of instrument 1450 includes an open channel that couples to endoscope 1410 via a rigid attachment segment on the shaft of the endoscope (e.g., rigid attachment segment 130 of adapter 100) as discussed above. The rigid attachment segment may be part of an adapter (e.g., adapter 100) that couples to a proximal part of the shaft of the endoscope 1480 or integrated into a proximal part of the shaft of the endoscope 1480. In this embodiment, instrument 1450 includes a handle mechanism 1455 to actuate tool tip 1470 attached to instrument shaft 1460. In this manner the instrument and scope are connected and the tool is actuated in a linear, streamlined manner (hand over top of the instrument instead of underneath) avoiding the need for a larger handle angled away from the scope. Additionally, this implementation has the advantage of not requiring a separate H-channel adapter. Rather, the upper channel for coupling to the endoscope is integrated into the instrument 1450.

Figure 10A:
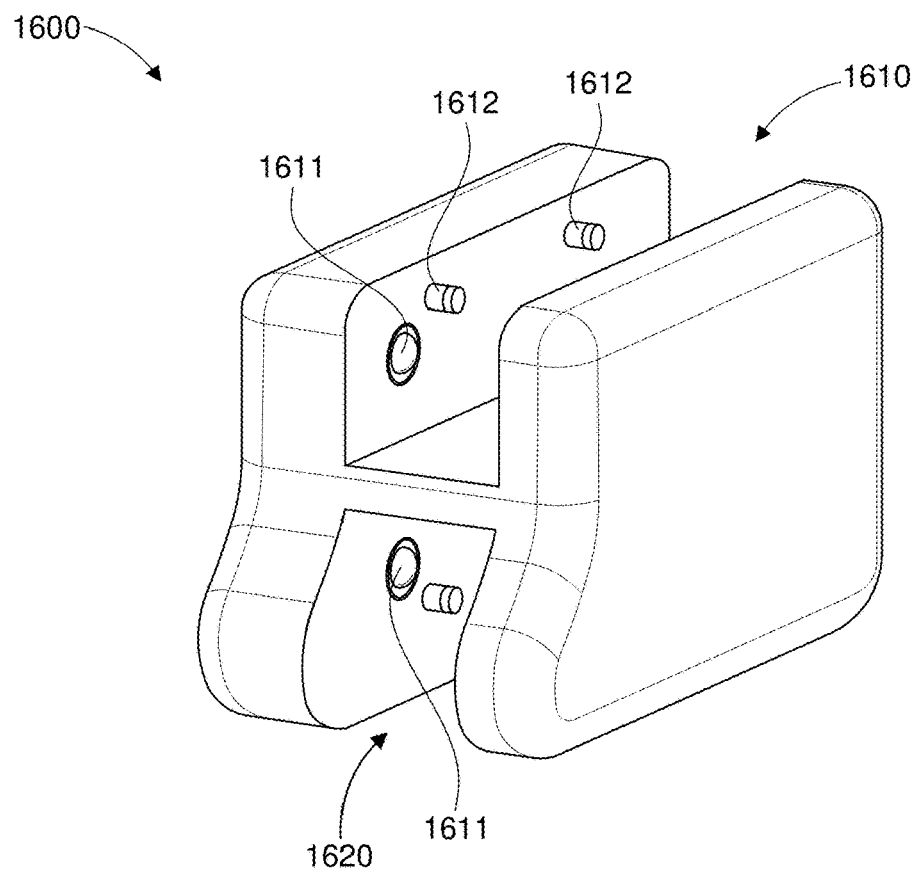
FIG. 10A shows a perspective view of an H-channel adapter that may be removably coupled to an endoscope attachment adapter and endoscope instrument tools, in accordance with some implementations of the disclosure.
Figure 10B:
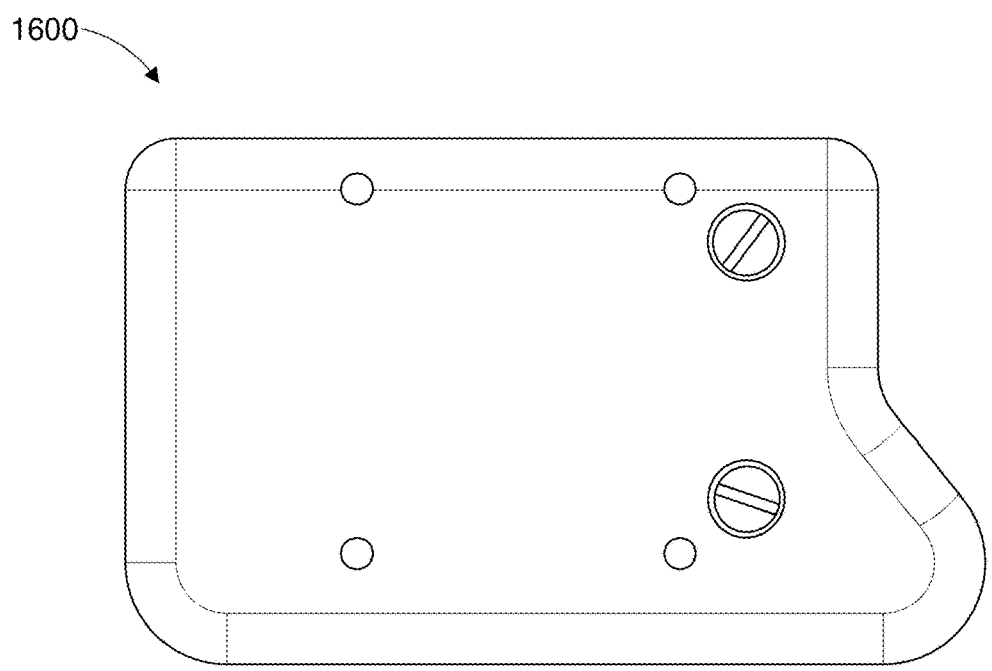
FIG. 10B shows a side view of the H-channel adapter of FIG. 10A.

FIGS. 10A-10B illustrates an H-channel adapter 1600 that may be removably coupled to an endoscope attachment adapter (e.g., adapter 100) and endoscope instrument tools, in accordance with implementations of the disclosure. As depicted, H-channel adapter 1600 includes an upper open channel 1610 for removably coupling H-channel adapter 1600 to an endoscope attachment adapter or to an instrument, and a lower open channel 1620, opposite the upper open channel 1610, for removably coupling H-channel adapter 1600 to an endoscope attachment adapter or to an instrument. In alternative implementations, there may be three or more channels integrated into the same adapter offset from one another at different angles. Such implementations would allow multiple instruments and/or endoscopes to be attached together at the same time.

The interior surface of the upper open channel 1610 includes ridges or protrusions 1612, and a spring-loaded protrusion (e.g., spring-loaded ball) 1611. Rigid attachment segment 130 may be secured in place by i) pushing it down into upper open channel 1610 along openings of two adjacent grooves 133; and ii) sliding rigid attachment segment 130 relative to open channel 1610 to position each ridge 1612 within a respective groove 133 of the adjacent grooves 133 such that protruding portions 138 of sections 131 adjacent the grooves 133 prevent lifting of the rigid attachment segment 130 (i.e., they block ridges 1612). Additionally, when the assembly is slid, spring-loaded protrusion 1611 may be secured within an indentation/hole 132 of the section 131 positioned next to the two grooves 133.

Like the upper open channel 1610, the interior surface of the lower open channel 1620 includes ridges or protrusions 1612, and a spring-loaded protrusion 1611. In alternative implementations, one or both of channels 1610 and 1620 may include at least two spring-loaded protrusions 1611. In alternative implementations, one or both of channels 1610 and 1620 may include an indentation or non-spring loaded protrusion in place of spring-load protrusion 1611.

Figure 11:
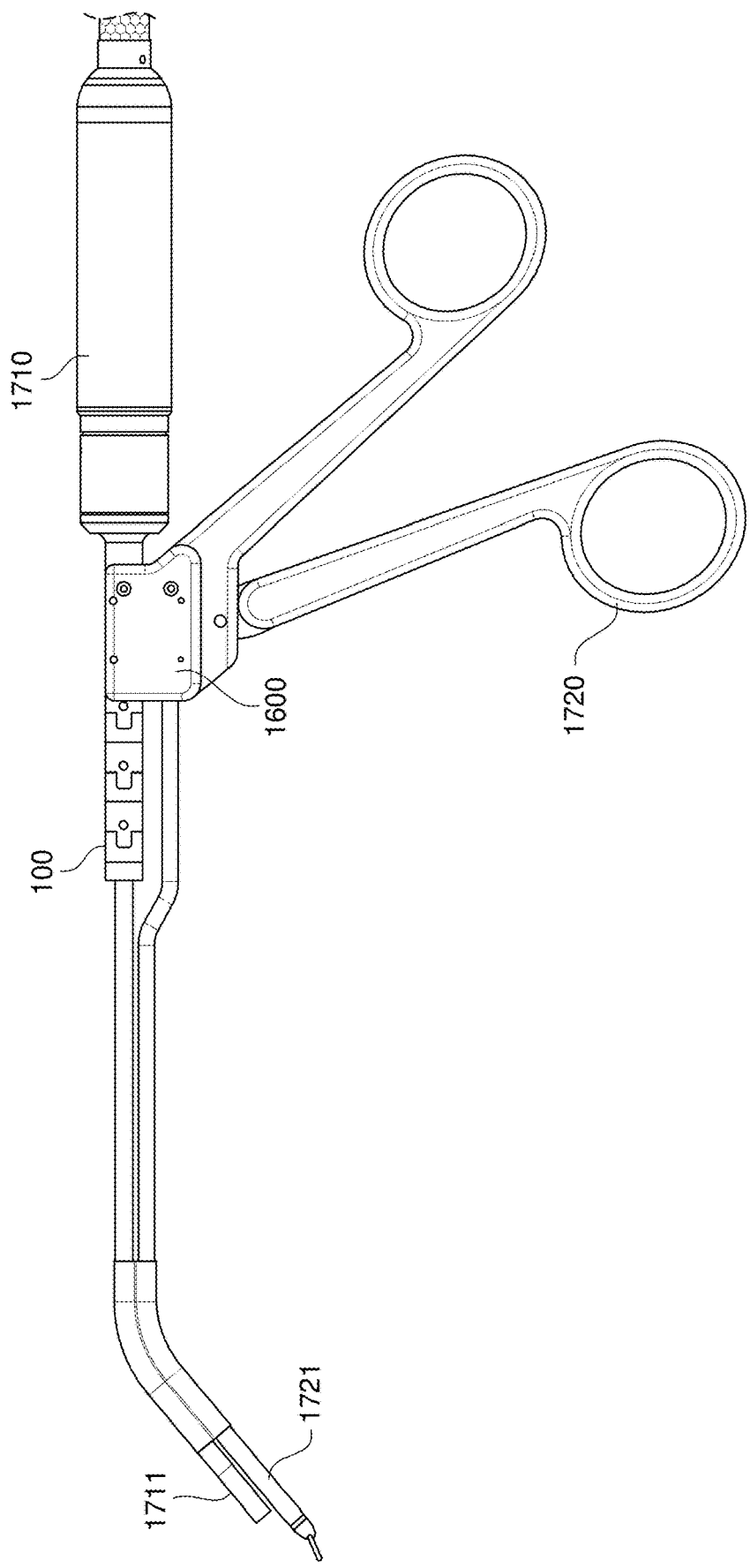
FIG. 11 shows a side view of an assembly including the H-channel adapter of FIG. 10A removably coupling an endoscope and forceps instrument, in accordance with some implementations of the disclosure.

FIG. 11 depicts an H-channel adapter 1600 used to removably couple an endoscope 1710 and forceps instrument 1720, in accordance with implementations of the disclosure. As depicted, the upper open channel 1610 of H-channel adapter 1600 is removably coupled to rigid attachment segment 130 of endoscope attachment adapter 100, and the lower open channel 1620 of H-channel adapter 1600 is removably coupled to a handle portion of forceps instrument 1720. By virtue of using H-channel adapter 1600 to removably couple endoscope 1710 to forceps instrument 1720, a distal portion 1711 of endoscope 1710 may be conveniently positioned adjacent tool portion 1721 of forceps instrument 1720 to capture a suitable image of a patient's cavity. Moreover, a variety of other instruments may be removably coupled to the lower channel 1620 of H-channel adapter 1600.

In certain implementations, it may be advantageous for the rigid proximal attachment segment (e.g., segment 130) of an endoscope adapter (e.g., adapter 100) threaded over a flexible shaft or endoscope shaft to include one or more hinges, allowing for changes in the shape of the endoscope shaft and adapter to accommodate varying shapes and contours of surgical instruments without allowing for flaccidity which would destabilize the scope when attached to an instrument. To this end, FIG. 12 depicts a portion of an endoscope shaft or attachment adapter 2300 that is rectangular and includes hinges 2310. In this implementation, hinges 2310 utilize an a joint that enables pivoting or rotation of portions of adapter 2300 about a single plane. FIG. 13 depicts a portion of an endoscope attachment adapter 2400 that is rectangular and includes a ball and socket hinge 2410. In this implementation, ball and socket hinge 2410 enables pivoting or rotation of portions of adapter 2400 about both a horizontal plane and vertical plane. Although FIGS. 12-13 illustrate two examples hinge joints that may be utilized, it should be appreciated that other suitable hinge joints may be used.

By virtue of utilizing a hinged adapter, different advantages may be realized depending on the instrument and application. For example, the head of the endoscope may be angled out of the way (e.g., 10-90 degrees) of the instrument. This may enable attachment of the endoscope to an instrument or device that itself must remain straight to function. As another example, the adapter may be hinged in two or three locations to bend the scope around the head of the instrument. Additionally, the hinged segments may enable attachment to various contours of instrumentation.

Figure 14A:
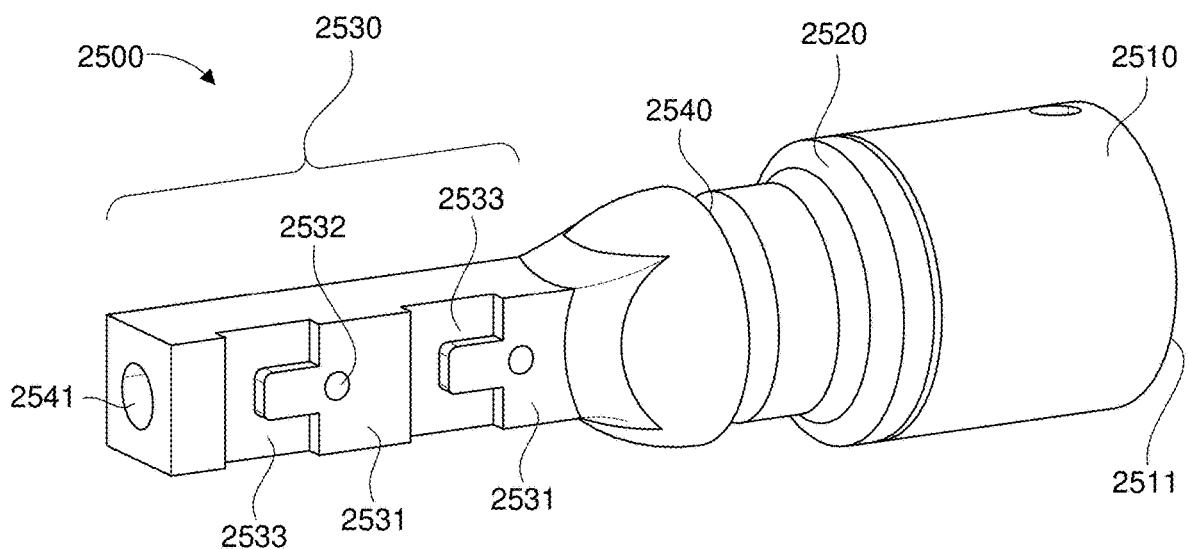
FIG. 14A shows a perspective view of another endoscope attachment adapter, in accordance with some implementations of the disclosure.
Figure 14B:
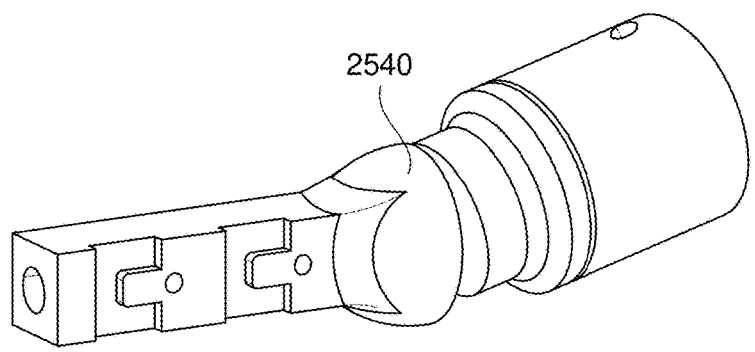
FIG. 14B shows a perspective view of the endoscope attachment adapter of FIG. 14A.
Figure 14C:
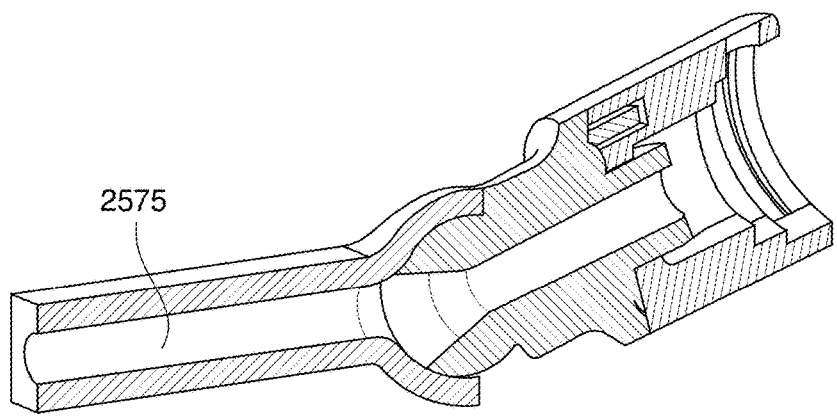
FIG. 14C shows a cross-sectional view of the endoscope attachment adapter of FIG. 14B.

FIGS. 14A-14C depict another embodiment of an endoscope attachment adapter 2500, in accordance with implementations of the disclosure. FIGS. 14A-14B illustrate a perspective view of adapter 2500, and FIG. 14C illustrates a cross-sectional view of adapter 2500. Adapter 2500 includes a coupler 2510, a rotatable joint 2520, a hinge joint 2540, and a rigid attachment segment 2530.

At a proximal end of adapter 2500 is an opening 2511 through connector 2510. At a distal end of adapter 2500 is an opening 2541. The opening 2541 may begin at a distal end of rigid attachment segment 2530. From opening 2511 to opening 2541 is a channel 2575 that extends through the length of adapter 2500. A flexible shaft of an endoscope may be threaded through channel 2575, starting at opening 2511 and moving through opening 2541. Once the endoscope shaft is threaded through the channel of adapter 2500, adapter 2500 may be secured at a proximal end of the endoscope shaft by removably coupling adapter connector 2510 (e.g., to an endoscope connector). The two connectors may be secured in a manner similar to that described above with reference to connector 110 of adapter 100.

Rigid attachment segment 2530 is four-sided with a square cross section. In other implementations, rigid attachment segment 2530 may have a different rectangular cross section or a circular cross-section. On the surface of one of the four sides of segment 2530 are formed a plurality of grooves/slots 2533 and a plurality of sections 2531 that protrude relative to the grooves 2533, each of the sections 2531 having a recessed indentation or hole 2532. Rigid attachment segment 2530 may be used to couple the adapter 2500 to an instrument in a manner similar to that discussed above with reference to adapter 100.

A rotatable joint 2520 positioned between hinge joint 2540 and coupler 2510 enables rotation of adapter 2500 about its longitudinal axis. Rotatable joint 2520 may be implemented in a manner similar to that discussed above with reference to rotatable joint 120. The hinge joint 2540 coupled between rigid attachment segment 2530 and coupler 2510 enables additional angling of rigid attachment segment 2530. By virtue of utilizing the combination of hinge joint 2540 and rotatable joint 2530 in this example, additional degrees of freedom in positioning adapter 2500 are provided. Adding several hinged joints 2540 in series allows for even greater changes in attachment shaft contour.

Figure 15A:
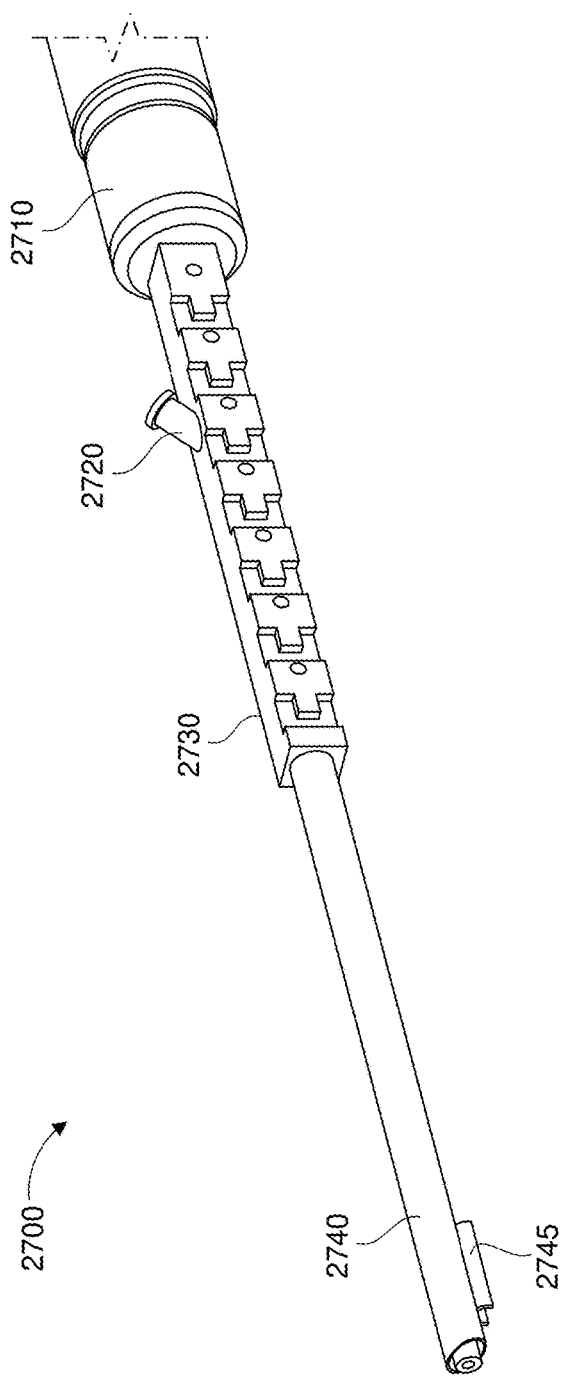
FIG. 15A shows a perspective view of an endoscope attachment adapter with an integrated cannula that may be used to flush or clean the tip of an endoscope, in accordance with some implementations of the disclosure.
Figure 15B:
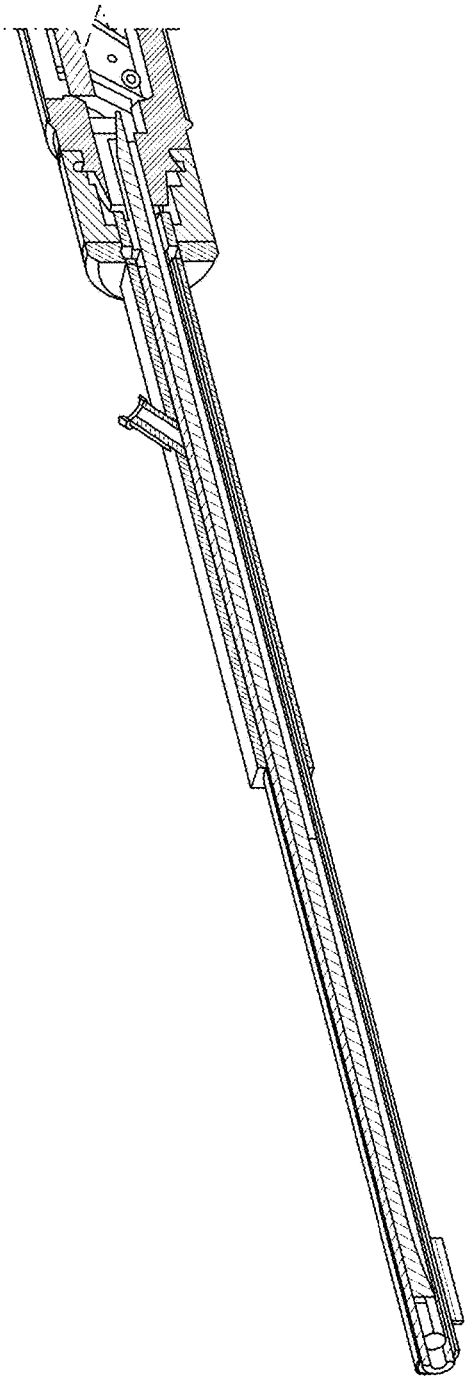
FIG. 15B shows a cross-sectional view of the endoscope attachment adapter of FIG. 15A.
Figure 16A:
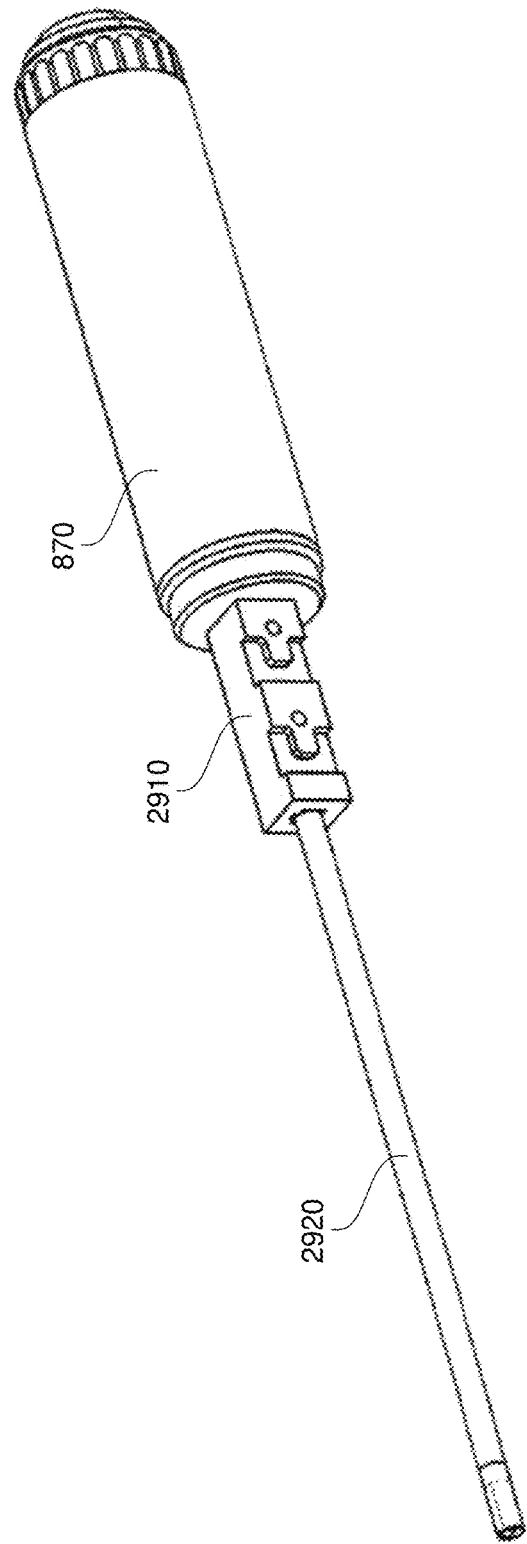
FIG. 16A shows a perspective view of an endoscope including a detachable endoscope shaft coupled to a rigid attachment segment, in accordance with some implementations of the disclosure.
Figure 16B:
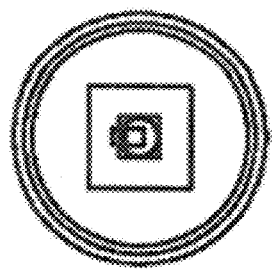
FIG. 16B shows a front view of the endoscope of FIG. 16A.

FIGS. 15A-15B show perspective and cross-sectional views of an endoscope attachment adapter 2700 with integrated cannula that may be used to flush/clean the tip of an endoscope. A suction/irrigation port 2720 would connect proximally via irrigation or suction tubing to a suction/irrigation pump activated by either foot or handheld control. On the distal undersurface of distal end 2740 of the cannula adapter 2700 there may be one or more instrument attachment connectors 2745 that are used to secure the adapter to an instrument shaft in one or more locations. Magnets incorporated within the cannula adapter or instrument shaft may also be used to attach the distal cannula adapter to the instrument shaft. In his example, the cannula adapter may slide over a rigid, flexible, or hybrid endoscope shaft and connect via connector 2710 to the endoscope coupler located on the distal endoscope housing, and may have rotation capabilities. The distal segment of the cannula, i.e., that portion of the cannula that extends distal from the rectangular attachment portion 2730 of the adapter, may also be rigid, flexible, or hybrid.

Although embodiments have thus far been primarily described in the context of endoscope attachment adapters that removably couple to an endoscope and/or instrument used with an endoscope, it should be appreciated that some of the adapter implementations described herein and their associated technical advantages may be realized by directly incorporating their features directly into an endoscope and/or endoscope instrument, whether disposable or reusable.

For example, a flexible-rigid hybrid endoscope (e.g., an endoscope having a shaft with a flexible distal end and a rigid proximal end) or a rigid endoscope (e.g., an endoscope having a rigid shaft) may have an endoscope shaft with an integrated proximal attachment segment similar in structural features to adapter 100, adapter 200, adapter 900, adapter 1000, adapter 2500, or adapter 2700. In such implementations, since the structural features of the adapter are incorporated into the endoscope (e.g., at the proximal end of the endoscope shaft), the endoscope connector (e.g., 110) of the adapter may be excluded.

For example, the proximal segment of the endoscope shaft may have a rectangular cross section, similar to the one described above for adapter 100, on which on at least one of the four sides are formed a plurality of grooves/slots 133 and a plurality of sections 131, each of the sections 131 having a recessed indentation or hole 132. In such implementations, the benefits of this top-down ratchet attachment design may be realized by directly integrating them into the proximal attachment segment of the endoscope shaft. Additionally, the endoscope shaft may be configured to rotate about a rotatable joint. Furthermore, the endoscope shaft may be configured to couple to instrument housing 1100, H-channel adapter 1300, or H-channel adapter 1600. Moreover, the proximal attachment segment of the endoscope shaft may itself include one or more hinges, allowing for changes in the shape of the endoscope shaft to accommodate varying shapes and contours of surgical instruments without allowing for flaccidity which would destabilize the scope when attached to an instrument.

FIGS. 16A-16D depict an endoscope housing 870 with a rigid, rectangular, proximal, attachment segment 2910 and a detachable endoscope shaft 2920, in accordance with some implementations of the disclosure. The proximal attachment segment 2910 may attach to instruments or adapters in a manner similar to that described above with reference to, for example, adapter 100. However, it is envisioned that other proximal attachment segments, as described above or otherwise, may be coupled to detachable endoscope shaft 2920.

As depicted by FIG. 16D, the detachable shaft 2920 is configured to be directly and removably inserted into the distal end of the proximal attachment segment 2910. In other configurations (not diagramed), the detachable shaft 2920 may include the rigid, rectangular, proximal attachment segment 2910. In such implementations, the combined distal and proximal shaft segments would removably insert into or onto the endoscope housing 870. Various lengths of the detachable endoscope shafts and contained segments are envisioned. In some implementations, the endoscope housing and/or endoscope shaft may be disposable. In other implementations, the detachable shaft may be specialized in a manner that alters its longitudinal configuration, distal or proximal instrument attachment mechanism, diameter, image resolution, number of cameras, angle of view, cross sectional shape (flat, circular, oval polygonal), flexibility, articulation, or internal channel or hardware configuration.

Figure 17A:
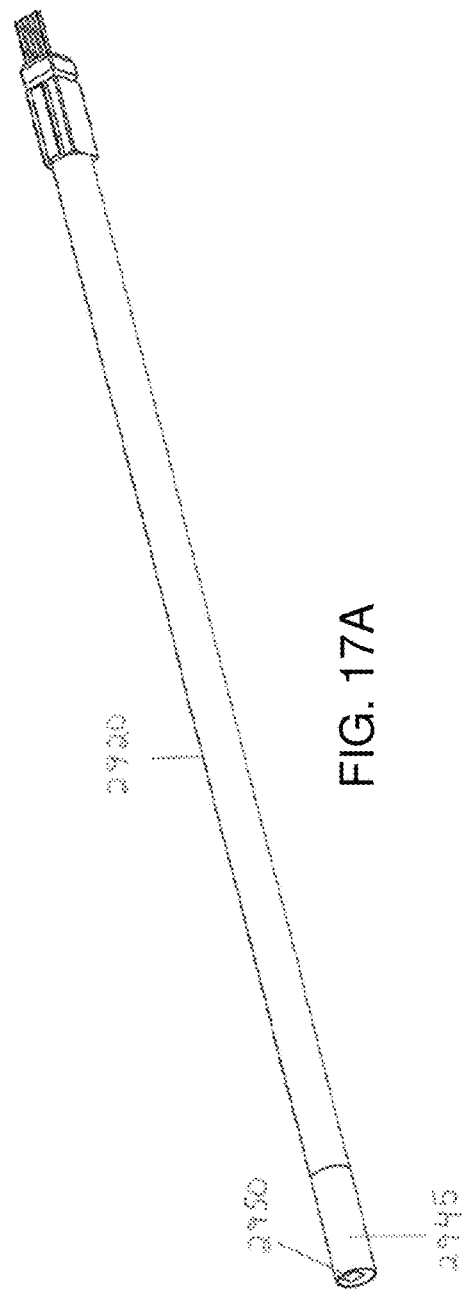
FIG. 17A shows a perspective view of a detachable endoscope shaft, in accordance with some implementations of the disclosure.
Figure 17B:
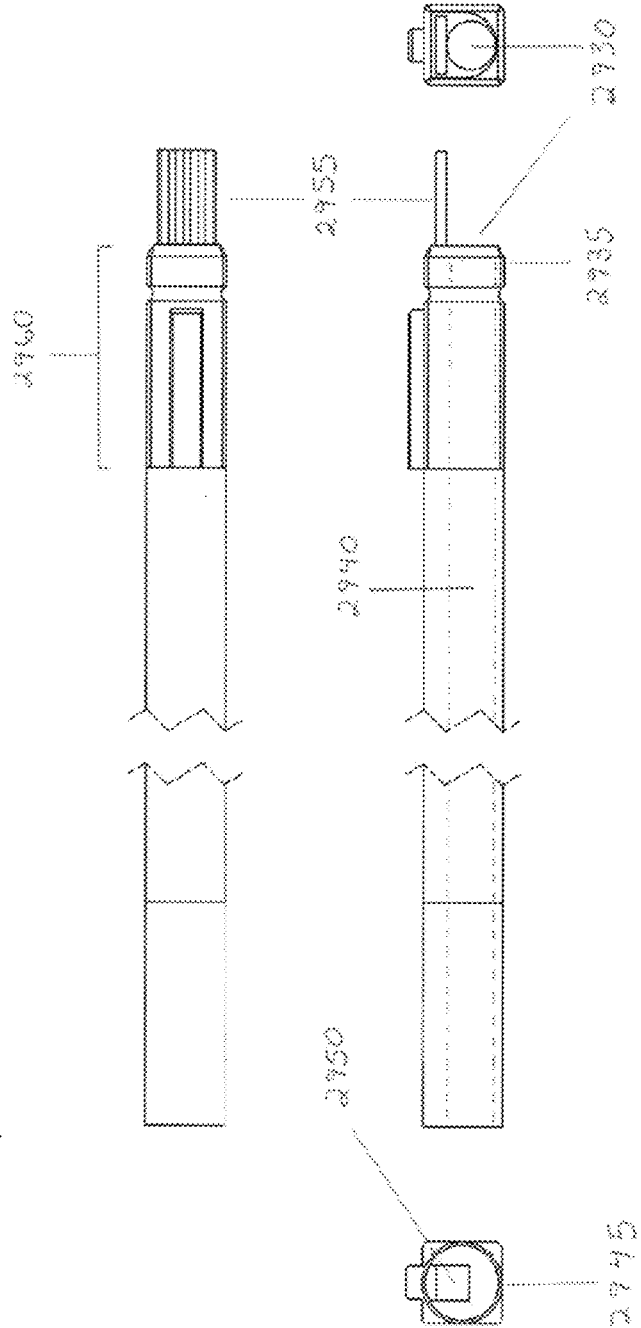
FIG. 17B shows multiple side views of the detachable endoscope shaft of FIG. 17A.
Figure 17D:
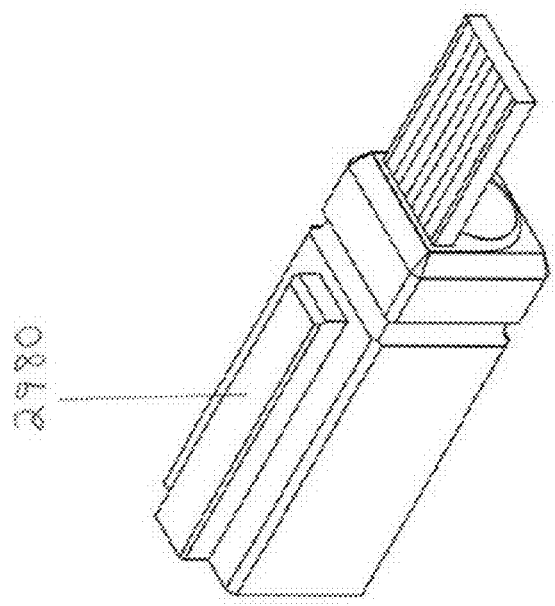
FIG. 17D shows a perspective view of the endoscope connector segment of the detachable endoscope shaft of FIG. 17A.
Figure 17F:
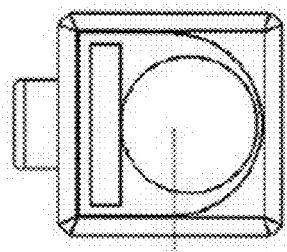
FIG. 17F shows a front view of an endoscope connector segment of the detachable endoscope shaft of FIG. 17A.
Figure 17C:
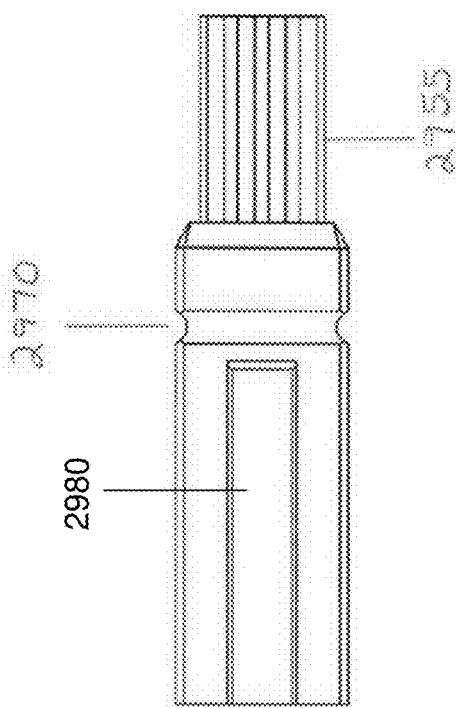
FIG. 17C shows a top view of an endoscope connector segment of the detachable endoscope shaft of FIG. 17A.
Figure 17E:
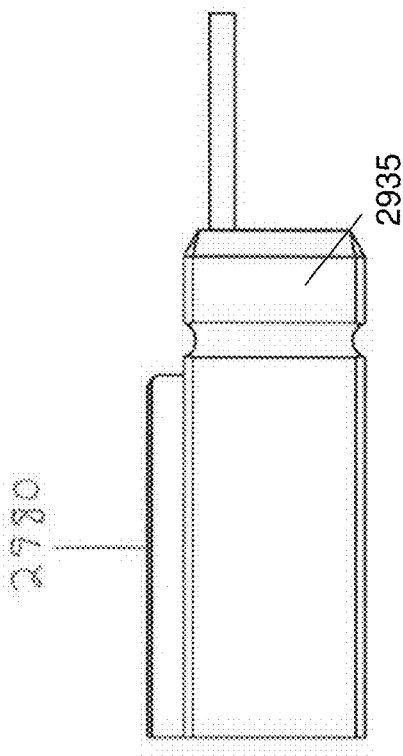
FIG. 17E shows a side view of the endoscope connector segment of the detachable endoscope shaft of FIG. 17A.

FIGS. 17A-17B depicts components of a detachable endoscope shaft 2920, in accordance with some implementations form the disclosure. During operation of the endoscope, light emitted from a light source (e.g., LED light source) contained within the endoscope housing 970 transmits through a proximal illumination coupling 2930 within the proximal end 2935 of the endoscope shaft 2920. The light travels through the shaft 2920 via an illumination channel 2940 that terminates at the distal segment 2945 of the shaft 2920. The illumination channel 2940 may be a molded illumination pipe or optical fibers. Alternatively, in other implementations (not illustrated) the light source may be integrated, internally and/or externally, into the detachable endoscope shaft 2920. In such implementations, the light source may be an LED alone or in combination with optical fibers positioned within or near the distal end of endoscope shaft 2920 (e.g., near the camera sensor 2950, in a different channel such that the light emitted by the light source does not interfere with the operation of the camera sensor), or in some other segment of the endoscope shaft 2920. Depending on the position of the light source in the detachable endoscope shaft 2920, such implementations may shorten or remove the illumination channel 2940 (e.g., molded illumination pipe). In order to supply power to the light source to make it operational in such implementations, the endoscope housing may provide power to the light source (and the image sensor) via a separate power line or via power-line communications.

A camera sensor 2950 located at the distal tip of the endoscope shaft 2920 electrically connects to a camera module connector 2955 located at the proximal end of the endoscope shaft. Just distal to the camera module connector 2955 is a scope connector segment 2960 that, along with the camera module connector 2955 inserts into the proximal rigid attachment segment 2910 extending from the endoscope housing 870 via an internal channel FIG. 18, 2975 to mechanically and electrically couple the endoscope shaft 2920 to endoscope housing 970.

FIGS. 17C-17F depict a larger scale view of the scope connector segment 2960. Within the proximal aspect of the scope connector segment 2960, just behind the camera module connector 2955, is a circumferential groove 2970 that allows for a snap-in connection to a female receptacle 2975 located on the distal aspect of the rigid proximal segment. An elongated rectangular protrusion 2980 rests along the top surface of the scope connector segment 2960 and acts to facilitate a keyed, one-way installation of the proximal endoscope shaft into the proximal rigid segment or endoscope housing. In other implementations, other protrusion(s) resting along a surface of the scope connector segment may facilitate installation. In still other implementations, the location of the elongated rectangular protrusion 2980 may be reversed and contained within the female receptacle 2975 and electrical contacts 2990 located on the proximal end of detachable shaft 2920.

Figure 18:
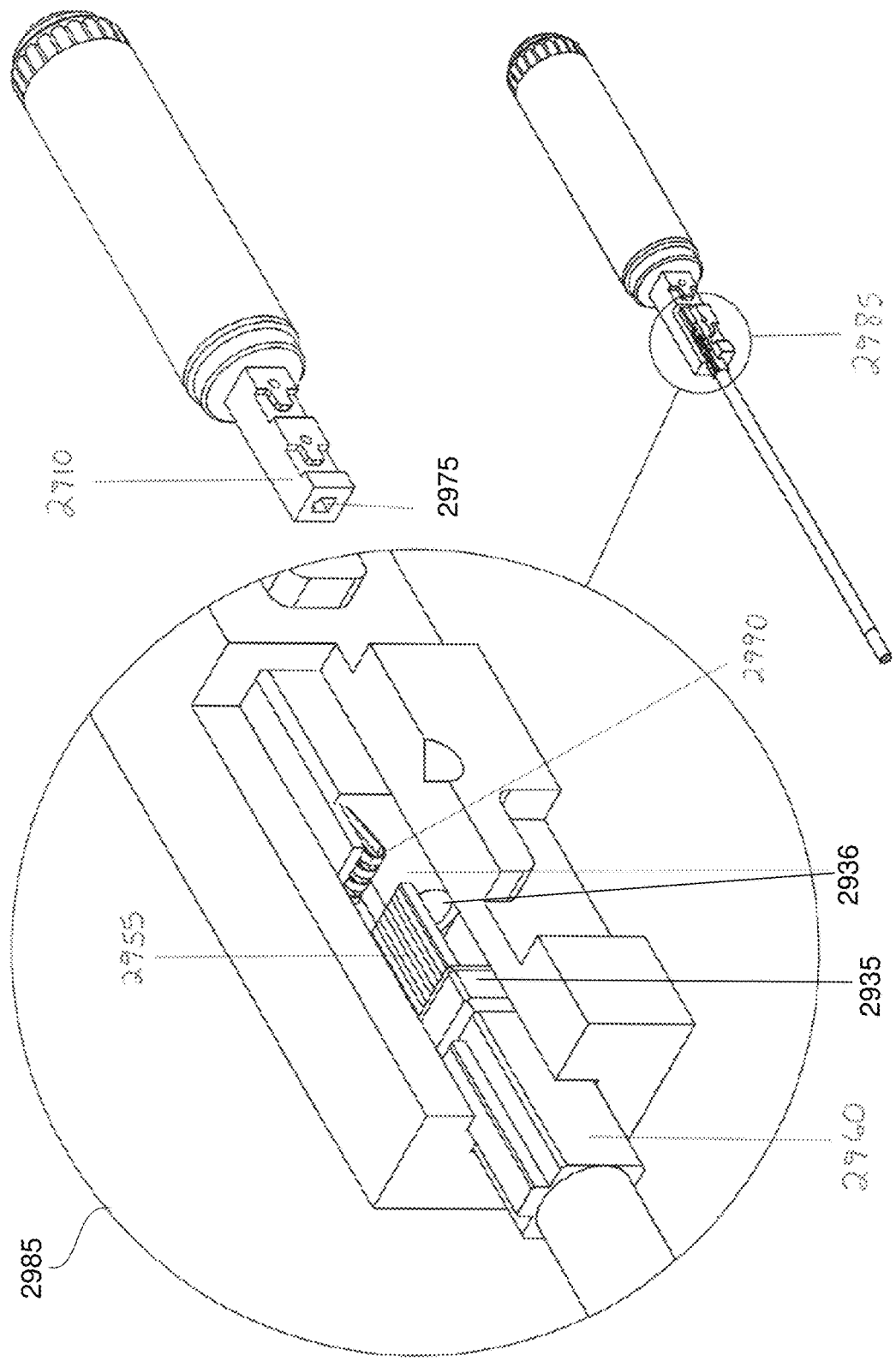
FIG. 18 shows an expanded, cross-sectional view of the mating connection between an endoscope connector segment of a detachable endoscope shaft and the distal end of a proximal attachment segment of the endoscope, in accordance with some implementations of the disclosure.

FIG. 18 shows an expanded, cross-sectional view of the mating connection 2985 between the detachable scope connector segment 2960 and the distal end of the proximal attachment segment 2910. As depicted, scope connector segment 2960 is inserted in female receptacle 2975 of proximal attachment segment 2910. During insertion, one or more electrical contacts 2990 within a camera module interface within the proximal attachment segment compress against one or more electrical contacts along the top surface of the inserted camera module connector 2955. Once the electrical connection is secured, camera signals (e.g., image data) collected via the camera sensor 2950 may travel to a processor located within the endoscope housing. Additionally, proximal illumination coupling 2930 within the proximal end 2935 is optically coupled to an illumination coupling 2936 in the interior of the proximal attachment segment. As such, after the optical connection, light emitted from a light source (e.g., LED light source) contained within the endoscope housing 970 transmits through illumination coupling 2936 and then through proximal illumination coupling 2930. Further, elongated rectangular protrusion 2980 mechanically couples into the proximal rigid segment. A spring-loaded ball or other protrusion (not seen) within the female receptacle could reversibly engage the circumferential groove 2970 to further secure the mechanical connection. As such, after the removable connection, the endoscope shaft 2920 may be electrically, optically, and mechanically coupled to the proximal attachment segment.

In configurations where the detachable shaft 2920 includes the proximal attachment segment 2910 (not illustrated herein), it should be appreciated that the illustrated connection components at the distal end of proximal attachment segment 2910 (e.g., electrical contacts 2990, female receptacle 2975, illumination coupling 2936, etc.) may instead be included in a distal end of endoscope housing 870. In such implementations, the detachable scope connector segment 2960 of shaft 2920 may be located proximal to the proximal attachment segment 2910.

In configurations where the light source is integrated into the detachable endoscope shaft 2920 (e.g., at the distal tip as one or more LEDs), the illumination couplings (e.g., illumination couplings 2930, 2936) may be omitted, and there is no need to optically couple the detachable endoscope shaft to the endoscope housing. In such cases, the endoscope housing 970 may provide power to the light source of the endoscope shaft when, for example, the endoscope shaft is electrically connected via connector 2955. In some cases, an additional connection may be used to supply power. The endoscope housing 970 may supply power via an integrated battery, an AC/DC power supply, or some other suitable power source.

FIGS. 19A-19B and 20A-20B illustrate two additional examples of electrical couplings that can be utilized to electrically couple a detachable endoscope shaft to a proximal attachment segment/endoscope housing, in accordance with some implementations of the disclosure. In these examples, the detachable endoscope shaft and endoscope housing are electrically coupled but not optically coupled.

Figure 19A:
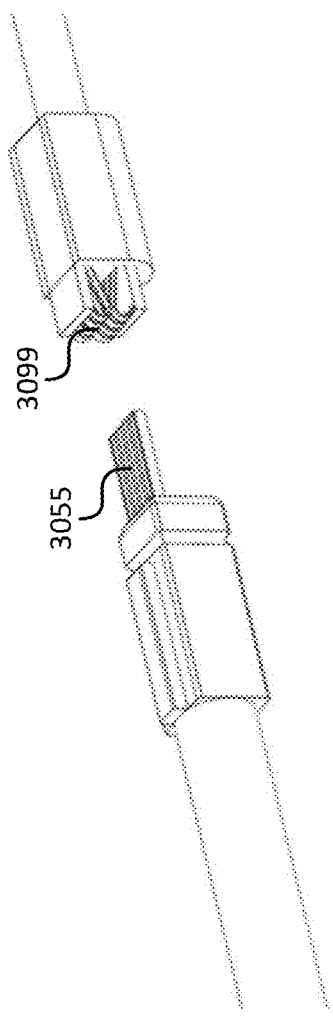
FIG. 19A illustrates electrical coupling between a detachable endoscope shaft and proximal attachment segment/endoscope housing using an internal, sliding contact, in accordance with some implementations of the disclosure.
Figure 19B:
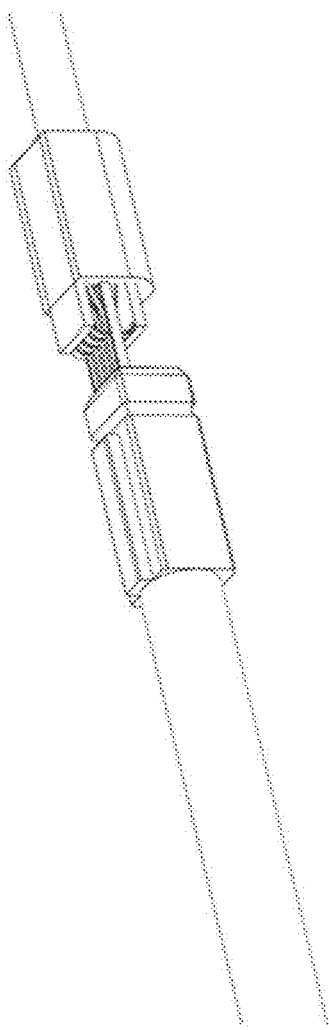
FIG. 19B illustrates electrical coupling between a detachable endoscope shaft and proximal attachment segment/endoscope housing using an internal, sliding contact, in accordance with some implementations of the disclosure.

FIGS. 19A-19B depict electrical coupling between a detachable endoscope shaft and proximal attachment segment/endoscope housing using an internal, sliding contact. During the mating connection between a detachable scope connector segment and the distal end of the proximal attachment segment or endoscope housing, one or more electrical contacts of a camera module connector 3055 located at a proximal end of the endoscope shaft slides between two sets of electrical contacts, one above and one below, of a camera module connector 3099 within the proximal attachment segment or endoscope housing. In this manner, multiple camera sensors arranged within or along shaft 2920 could be powered and signals transmitted simultaneously to the endoscope housing. It should be noted that other configurations for electrical connections of connector 2955 are envisioned. Such configurations, such as circular, oval, cross-shaped, T-shaped, etc., could allow for three or more camera modules connected simultaneously.

Figure 20A:
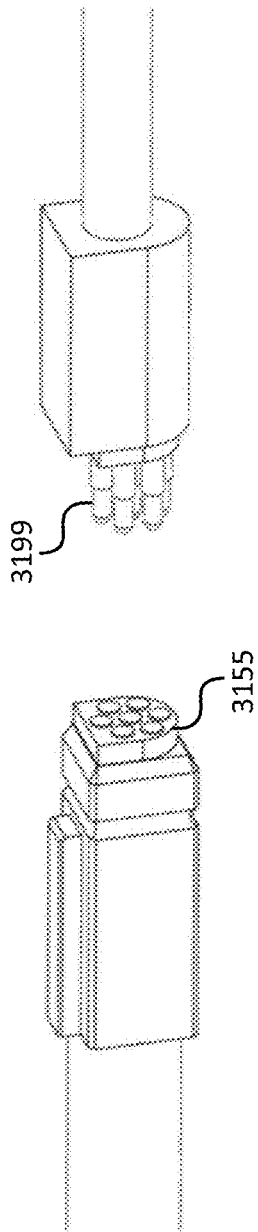
FIG. 20A illustrates electrical coupling between a detachable endoscope shaft and proximal attachment segment/endoscope housing using an internal, compression contact, in accordance with some implementations of the disclosure.
Figure 20B:
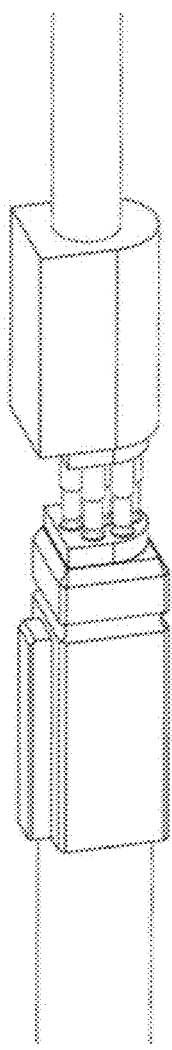
FIG. 20B illustrates electrical coupling between a detachable endoscope shaft and proximal attachment segment/endoscope housing using an internal, compression contact, in accordance with some implementations of the disclosure.

FIGS. 20A-20B depict electrical coupling between a detachable endoscope shaft and proximal attachment segment/endoscope housing using an internal, pogo compression contact. During the mating connection between a detachable scope connector segment and the distal end of the proximal attachment segment or endoscope housing, one or more electrical contacts of a camera module connector 3199 within the proximal attachment segment or endoscope housing, are compressed against one or more electrical contacts of a camera module connector 3155 located at a proximal end of the endoscope shaft. Although this example shows male electrical contacts on camera module connector 3199 inserted into corresponding female electrical contacts of camera module connector 3155, the female and male electrical contacts can be reversed.

FIGS. 21A-21D depict an endoscope including an endoscope housing 3270 and detachable endoscope shaft 3220 configured to be removably coupled, in accordance with some implementations of the disclosure. In this example, the endoscope housing 3270 and detachable endoscope shaft 3220 are configured to be mechanically, electrically, and optically coupled.

The detachable endoscope shaft 3220 includes a distal segment 3221, a proximal attachment segment 3222, and a scope connector segment 3230 proximal to the proximal attachment segment 3222. The proximal attachment segment 3222 may attach to instruments or adapters in a manner similar to that described above. The scope connector segment 3230 is configured to removably, electrically, optically, and mechanically couple to an endoscope housing connector segment 3280 that is on a distal end of endoscope housing 3270. This coupling is illustrated in further detail by FIGS. 21C-21D.

During coupling, endoscope housing connector segment 3280 is inserted into an opening of scope connector segment 3230. The endoscope housing connector segment 3280 includes a groove 3282 that slidably receives an elongated rectangular protrusion/bar 3322 in an interior of scope connector segment 3230, which helps secure the mechanical connection between the detachable endoscope shaft 3220 and endoscope housing 3270.

During insertion, one or more electrical contacts 3281 on an underside of endoscope housing connector segment electrically couple to one or more electrical contacts 3231 in an interior of scope connector segment 3230. Once the electrical connection is secured, image signals (e.g., image data) may travel between endoscope shaft 3220 and endoscope housing 3270. In implementations where one or more image sensors or LEDs are within detachable endoscope shaft 3220 (e.g., near a distal end of distal segment 3221), image signals collected via the image sensor(s) can travel to endoscope housing 3270 for further processing. In a similar manner, electrical power can be transmitted distally to power any LEDs withing the endoscope shaft. In implementations where detachable endoscope shaft 3220 includes multiple image sensors, separate sets of electrical contacts located on each segment 3230, 3280 can be used to respectively couple the signal(s) from each image sensor. For example, where two image sensors are included, the scope connector segment 3230 can include two sets of electrical contacts (e.g., top row and bottom row of contacts 3231) that couple to two respective sets of electrical contacts of endoscope housing connector segment 3280 (e.g., top row and bottom row of contacts 3281). Various other electrical configurations are also envisioned.

Figure 21A:
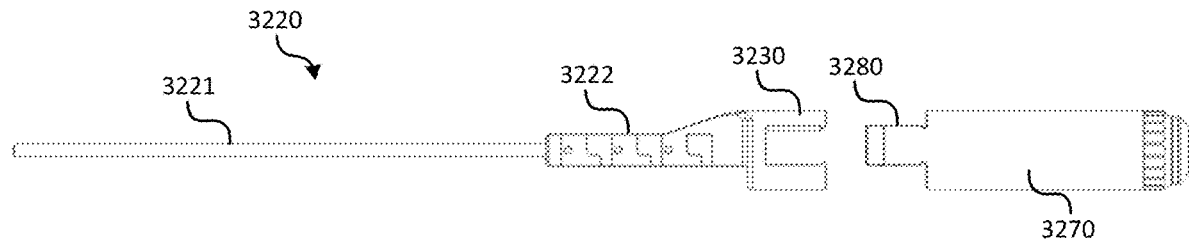
FIG. 21A shows a side view of an endoscope including an endoscope housing and detachable endoscope shaft configured to be removably coupled, in accordance with some implementations of the disclosure.
Figure 21B:
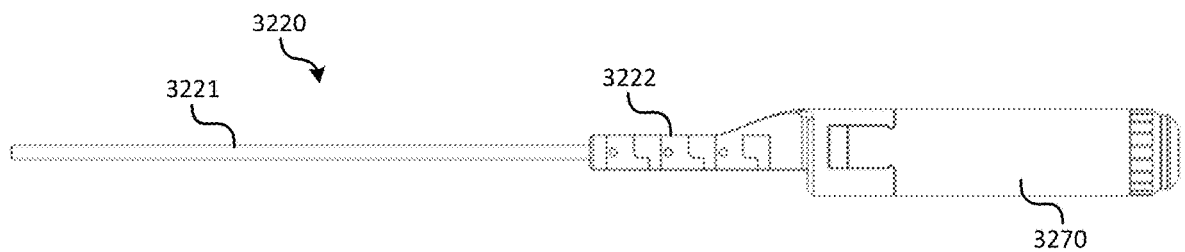
FIG. 21B shows the endoscope of FIG. 21A after the endoscope housing and detachable endoscope shaft are removably coupled.
Figure 21C:
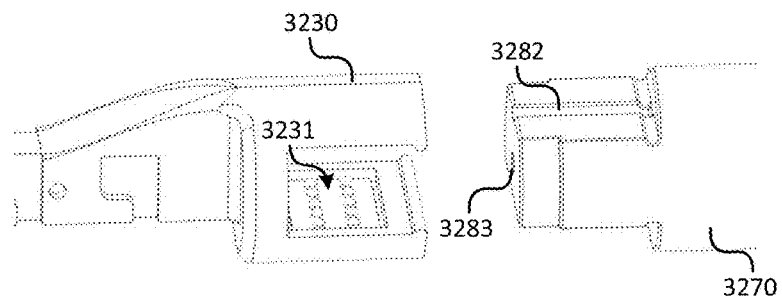
FIG. 21C shows a perspective view of the connector segments of the endoscope housing and detachable endoscope shaft of FIG. 21A.
Figure 21D:
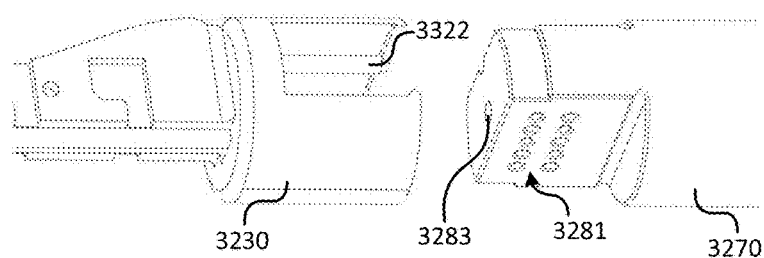
FIG. 21D shows another perspective view of the connector segments of the endoscope housing and detachable endoscope shaft of FIG. 21A.

Also illustrated in FIGS. 21C-21D is an illumination coupling 3283 of endoscope housing connector segment 3280 that is optically coupled to an illumination coupling (not shown) of scope connector segment 3230. As such, after the optical connection, light emitted from a light source (e.g., LED light source) contained within the endoscope housing 3270 transmits through illumination coupling 3283 and then through detachable endoscope shaft 3220 (e.g., via an illumination channel that terminates at the distal end of shaft 3220).

As depicted, the profile of the endoscope housing connector 3280 of the endoscope housing 3270 provides a relatively easy surface to clean post operation, thereby improving the utility and ergonomics of the endoscope assembly.

In alternative implementations, endoscope shaft 3220 can contain optical fibers for image delivery from endoscope shaft 3220 to one or more image sensors contained within endoscope housing 3270. In such implementations, the electrical connection can be optionally omitted and replaced by a fiber optical connection between segments 3230 and 3280 (e.g., contacts 3231 and 3281 are replaced by a fiber optical coupling component on each connector). Alternatively, the electrical connection can be maintained only for the purpose of supplying power from the endoscope housing 3270 to one or more light sources and/or other components of endoscope shaft 3220.

Figure 22A:
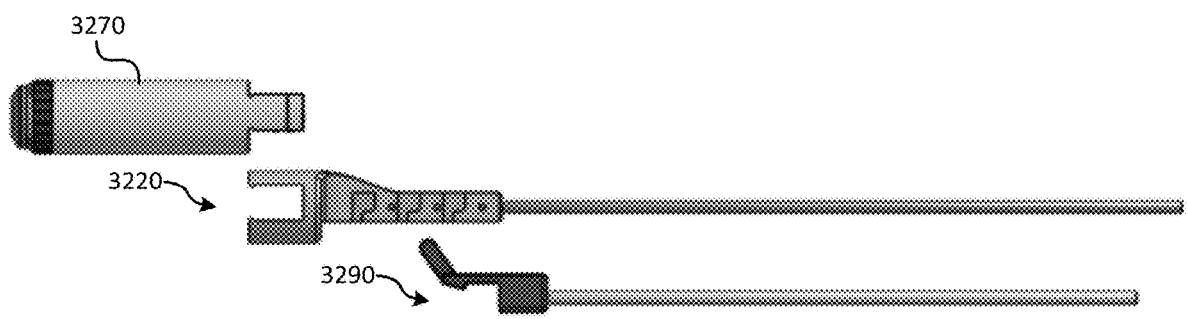
FIG. 22A shows a removable endoscope shaft assembly including an endoscope housing, detachable endoscope shaft, and sleeve adapter, in accordance with some implementations of the disclosure.
Figure 22B:
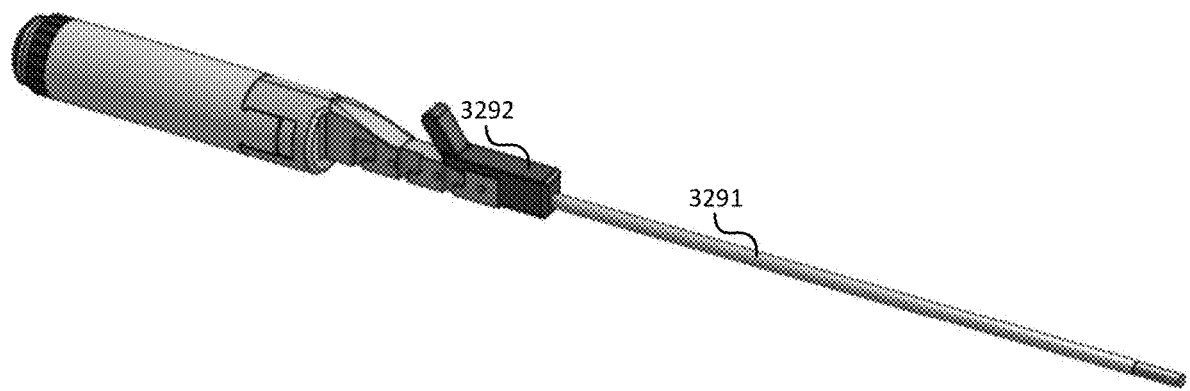
FIG. 22B shows the removable endoscope shaft assembly of FIG. 22A after the endoscope housing, detachable endoscope shaft, and sleeve adapter are coupled together.

In some implementations, the utility and/or configurability of the endoscope with detachable shaft can be further expanded using additional mechanical attachment mechanisms or adapters. For example, FIGS. 22A-22B depict a removable endoscope shaft assembly including endoscope housing 3270, detachable endoscope shaft 3220, and sleeve adapter 3290. The sleeve adapter 3290 includes a cannula 3291 and connector 3292. The sleeve adapter 3291 can be removably coupled to detachable endoscope shaft 3220 by sliding the distal segment 3221 through an opening/channel running from connector 3292 through cannula 3291, and securing connector 3292 to proximal attachment segment 3222. In some implementations, during operation, sleeve adapter 3291 can function as a straight, curved, or irregularly configured stiffening cannula that facilitates guiding of a flexible endoscope shaft with or without an instrument attached to the attachment segment. The cannula 3291 can be malleable or magnetic.

During operation, sleeve adapter 3291 can function as a stiffening cannula that facilitates guiding of a flexible endoscope shaft. The cannula 3291 can be malleable.

Figure 23A:
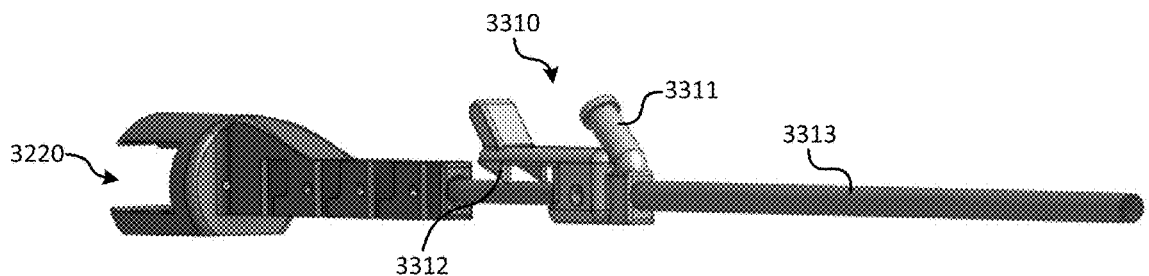
FIG. 23A shows an irrigation or suction sleeve adapter being removably coupled to a detachable endoscope shaft, in accordance with some implementations of the disclosure.
Figure 23B:
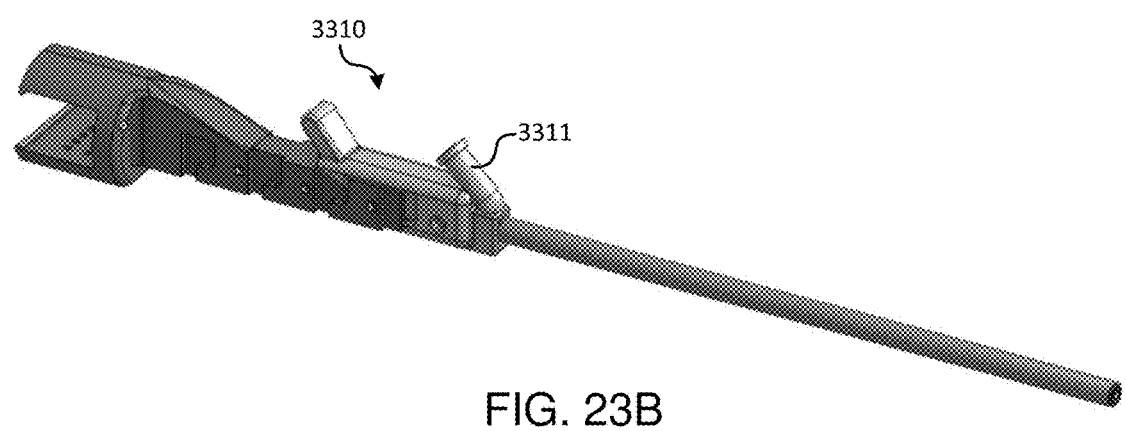
FIG. 23B shows an irrigation or suction sleeve adapter of FIG. 23A after it is removably coupled to the detachable endoscope shaft of FIG. 23A.

FIGS. 23A-23B depict an irrigation or suction sleeve adapter 3310 removably coupled to a detachable endoscope shaft 3220, in accordance with some implementations of the disclosure. The irrigation or suction sleeve adapter 3310 adds an additional irrigation and/or suction capability through cannula 3313 that is slid over distal segment 3221. The cannula 3313 can be used to flush/clean the tip of endoscope shaft 3320. A suction/irrigation port 3311 would connect proximally via irrigation or suction tubing to a suction/irrigation pump activated by either foot or handheld control. The irrigation or suction sleeve adapter 3310 can be secured to detachable endoscope shaft 3220 by coupling one or more connectors 3312 of adapter 3310 to proximal attachment segment 3222.

Figure 24:
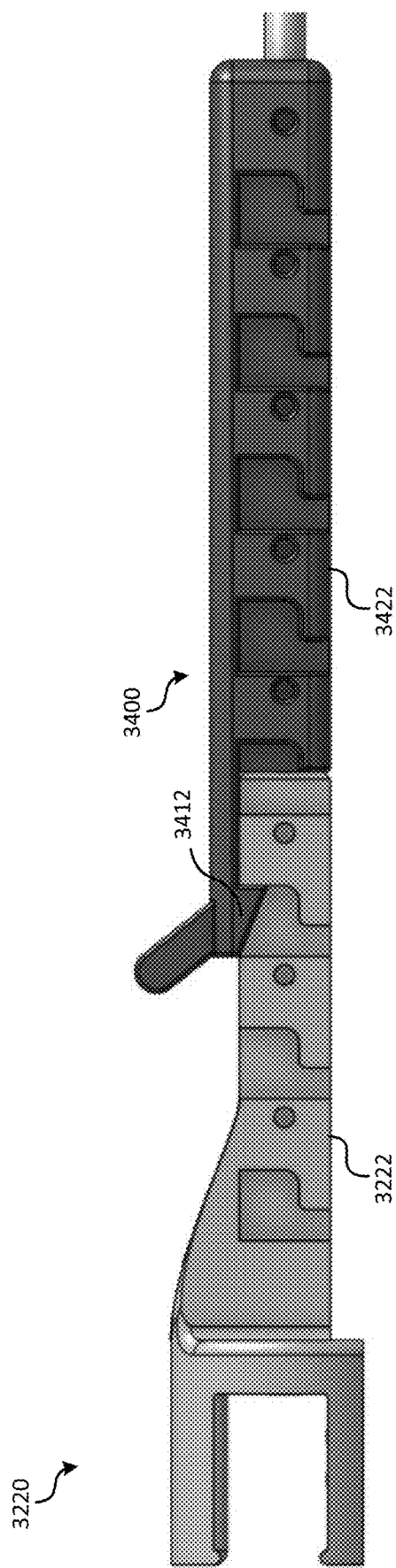
FIG. 24 depicts an attachment segment extension adapter removably coupled to a detachable endoscope shaft, in accordance with some implementations of the disclosure.

FIG. 24 depicts an attachment segment extension adapter 3400 removably coupled to a detachable endoscope shaft 3220, in accordance with some implementations of the disclosure. After adapter 3400 is secured to detachable endoscope shaft 3220 by coupling one or more connectors 3412 of adapter 3400 to proximal attachment segment 3222, the features of proximal attachment segment 3222 can be extended by corresponding features in attachment segment 3422 of adapter 3400, thereby providing additional flexibility (e.g., lengthwise positioning) to attach instruments or adapters as described above.

The endoscopes, attachment mechanisms, and instruments described herein may be utilized in any suitable application. For example, they may be utilized in Otorhinolaryngologic (Ear, nose, and throat, ENT) surgical applications. They may also be utilized in other surgical and medical specialties such as general surgery, gastroenterology, pulmonology, urology, plastic surgery, neurosurgery, OB/GYN, and orthopedics for applications such as surgical stapling, tissue ablation, arthroscopic surgery, etc. Commercial, non-surgical, applications for the technology disclosed herein are also applicable.

Although described above in terms of various example implementations, it should be understood that the various features, aspects and functionality described in one or more of the individual implementations are not limited in their applicability to the particular implementation with which they are described, but instead can be applied, alone or in various combinations, to one or more of the other implementations of the application, whether or not such implementations are described and whether or not such features are presented as being a part of a described implementation. Thus, the breadth and scope of the present application should not be limited by any of the above-described example implementations.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

To the extent applicable, the terms "first," "second," "third," etc. herein are merely employed to show the respective objects described by these terms as separate entities and are not meant to connote a sense of chronological order, unless stated explicitly otherwise herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide some instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various implementations set forth herein are described in terms of example block diagrams, flow charts and other illustrations. As will become apparent to one of ordinary skill in the art after reading this document, the illustrated implementations and their various alternatives can be implemented without confinement to the illustrated examples. For example, block diagrams and their accompanying description should not be construed as mandating a particular architecture or configuration.

While various implementations of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various implementations be implemented to perform the recited functionality in the same order unless the context dictates otherwise.

What is claimed is:

1. An endoscope assembly, comprising:
   an endoscope housing comprising a distal connector including first circuitry, the first circuitry configured to supply power from the endoscope housing or receive one or more image signals; and
   a detachable endoscope shaft comprising:
   a distal segment configured to be inserted in a patient cavity;
   a rigid attachment segment proximal to the distal segment, the rigid attachment segment configured to be removably coupled to an instrument or adapter; and
   a proximal connector configured to removably and electrically couple to the distal connector, the proximal connector including second circuitry configured to electrically couple to the first circuitry.

2. The endoscope assembly of claim 1, wherein:
   the detachable endoscope shaft further comprises one or more image sensors configured to generate the one or more image signals;
   the second circuitry is configured to transmit the one or more image signals to the first circuitry; and
   the first circuitry is configured to receive the one or more image signals.

3. The endoscope assembly of claim 2, wherein:
   the one or more image signals comprise a first image signal and a second image signal;
   the one or more image sensors comprise a first image sensor configured to generate the first image signal and a second image sensor configured to generate the second image signal;
   the first circuitry comprises one or more first electrical contacts configured to receive the first image signal and one or more second electrical contacts configured to receive the second image signal;
   the second circuitry comprises one or more third electrical contacts configured to transmit the first image signal and one or more fourth electrical contacts configured to transmit the second image signal;
   the one or more first electrical contacts and the one or more third electrical contacts are configured to removably couple; and
   the one or more second electrical contacts and the one or more fourth electrical contacts are configured to removably couple.

4. The endoscope assembly of claim 1, wherein the first circuitry comprises first and second sets of opposing electrical contacts, and the second circuitry comprises a third set of electrical contacts configured to slidably connect between the first and second sets of opposing electrical contacts.

5. The endoscope assembly of claim 1, wherein:
   the endoscope housing further comprises a light source; and
   the distal connector is configured to optically couple the light source to the detachable endoscope shaft via the proximal connector.

6. The endoscope assembly of claim 5, wherein the distal connector further includes a groove or protrusion configured to mechanically couple the distal connector to the proximal connector.

7. The endoscope assembly of claim 5, wherein the detachable endoscope shaft further comprises an illumination channel that begins at a first opening at a proximal end of the detachable endoscope shaft, the illumination channel configured to pass light emitted by the light source.

8. The endoscope assembly of claim 1, further comprising a sleeve adapter configured to removably couple to the detachable endoscope shaft, the sleeve adapter comprising:
   a proximal connector configured to couple to the rigid attachment segment; and
   a cannula distally extending from the proximal connector, the distal segment configured to slide through the cannula when the sleeve adapter is removably coupled to the detachable endoscope shaft.

9. The endoscope assembly of claim 8, wherein the cannula of the sleeve adapter is stiffer than the distal segment, the cannula configured to facilitate guiding the detachable endoscope shaft.

10. The endoscope assembly of claim 8, wherein the sleeve adapter further comprises a suction or irrigation port coupled to an inside of the cannula.

11. The endoscope assembly of claim 8, wherein:
    the rigid attachment segment comprises first repeating features configured to couple to the instrument or the adapter in one or more lengthwise positions; and
    the sleeve adapter further comprises second repeating features configured to couple to the instrument or the adapter in one or more additional lengthwise positions.

12. The endoscope assembly of claim 1, wherein:
    the distal segment comprises one or more light sources; and
    when the first circuitry is electrically coupled to the second circuitry, the first circuitry is configured to supply power from the endoscope housing to the detachable endoscope shaft to power the one or more light sources.

13. The endoscope assembly of claim 1, wherein: a surface of the rigid attachment segment comprises a groove and a section adjacent the groove, the section protruding relative to the groove and comprising a recessed indentation or protrusion.

14. The endoscope assembly of claim 13, wherein:
    the rigid attachment segment is configured to removably couple to a channel of the instrument or the adapter;
    the groove is configure to couple to a first protrusion of the channel; and the recessed indentation is configured to couple to a second protrusion of the channel.

15. The endoscope assembly of claim 1, wherein:
a surface of the rigid attachment segment comprises multiple grooves and multiple sections alternating along a longitudinal length of the rigid attachment segment;
each of the sections protrudes relative to the grooves and comprises a recessed indentation or protrusion; and
the multiple sections and the multiple grooves are configured such that the instrument or the adapter can be coupled to the detachable endoscope shaft in a plurality of lengthwise positions.

16. The endoscope assembly of claim 1, wherein:
the detachable endoscope shaft further comprises optical fibers configured to transmit an image signal; and
the proximal connector is further configured to fiber optically couple to the distal connector.

17. A detachable endoscope shaft comprising:
a distal segment configured to be inserted in a patient cavity;
a rigid attachment segment proximal to the distal segment, the rigid attachment segment configured to be removably coupled to an instrument or adapter; and
a proximal connector configured to removably and electrically couple to a distal connector of an endoscope housing, the proximal connector including first circuitry configured to electrically couple to second circuitry of the distal connector.

18. The detachable endoscope shaft of claim 17, further comprising:
a first image sensor configured to generate a first image signal; and
a second image sensor configured to generate a second image signal,
wherein:
the first circuitry comprises one or more first electrical contacts configured to receive the first image signal and one or more second electrical contacts configured to receive the second image signal;
the one or more first electrical contacts are configured to removably couple to one or more third electrical contacts of the second circuitry; and
the one or more second electrical contacts are configured to removably couple to one or more fourth electrical contacts of the second circuitry.

19. The detachable endoscope shaft of claim 17, wherein:
a surface of the rigid attachment segment comprises a groove and a section adjacent the groove, the section protruding relative to the groove and comprising a recessed indentation or protrusion.

20. The detachable endoscope shaft of claim 17, wherein:
a surface of the rigid attachment segment comprises multiple grooves and multiple sections alternating along a longitudinal length of the rigid attachment segment;
each of the sections protrudes relative to the grooves and comprises a recessed indentation or protrusion; and
the multiple sections and the multiple grooves are configured such that the instrument or the adapter can be coupled to the detachable endoscope shaft in a plurality of lengthwise positions.

* * * * *